(12) United States Patent
Steinke et al.

(10) Patent No.: US 10,960,214 B2
(45) Date of Patent: Mar. 30, 2021

(54) SYSTEMS AND METHODS FOR CONTROLLING ELECTRICAL STIMULATION USING MULTIPLE STIMULATION FIELDS

(71) Applicant: Boston Scientific Neuromodulation Corporation, Valencia, CA (US)

(72) Inventors: G. Karl Steinke, Valencia, CA (US); Stephen Carcieri, Los Angeles, CA (US); Richard Mustakos, Simi Valley, CA (US); Hemant Bokil, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 226 days.

(21) Appl. No.: 16/049,587

(22) Filed: Jul. 30, 2018

(65) Prior Publication Data
US 2019/0054306 A1    Feb. 21, 2019

Related U.S. Application Data

(60) Provisional application No. 62/545,855, filed on Aug. 15, 2017.

(51) Int. Cl.
*A61N 1/372*    (2006.01)
*A61N 1/05*    (2006.01)
*A61N 1/36*    (2006.01)

(52) U.S. Cl.
CPC ....... *A61N 1/37247* (2013.01); *A61N 1/0551* (2013.01); *A61N 1/3605* (2013.01);
(Continued)

(58) Field of Classification Search
CPC .................................................. A61N 1/37247
See application file for complete search history.

(56) References Cited

U.S. PATENT DOCUMENTS

| 3,999,555 A | 12/1976 | Person |
| 4,144,889 A | 3/1979 | Tyers et al. |

(Continued)

FOREIGN PATENT DOCUMENTS

| EP | 1048320 | 11/2000 |
| EP | 1166819 | 1/2002 |

(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.

(Continued)

*Primary Examiner* — George R Evanisko
(74) *Attorney, Agent, or Firm* — Branch Partners PLLC; Bruce E. Black

(57) ABSTRACT

A system for programming electrical stimulation by a lead includes a processor coupled to a display. The processor presents an interface on the display with user-selectable controls to define stimulation fields and repeating stimulation patterns for delivering the stimulation fields temporally-coordinated with each other. The user-selectable controls include a field control to define the number of stimulation fields, a location control to define locations of the stimulation fields relative to the lead, a repetition control to define a repetition frequency of the stimulation patterns, and a temporal-adjustment control to define temporal adjustments of the stimulation fields. The processor also receives selections of the user-selectable controls to define the stimulation fields and the repeating stimulation patterns; and initiate a signal that provides a pulse generator with instructions that enable the pulse generator to generate the stimulation fields according to the repeating stimulation patterns using the lead coupled to the pulse generator.

20 Claims, 12 Drawing Sheets

(52) U.S. Cl.
CPC ..... *A61N 1/36171* (2013.01); *A61N 1/36175* (2013.01); *A61N 1/36185* (2013.01)

(56) References Cited

U.S. PATENT DOCUMENTS

| | | | |
|---|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman et al. |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sande et al. |
| 6,351,675 B1 | 2/2002 | Tholen et al. |
| 6,353,762 B1 | 3/2002 | Baudino et al. |
| 6,366,813 B1 | 4/2002 | DiLorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schram et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant |
| 7,177,674 B2 | 2/2007 | Echauz et al. |
| 7,181,286 B2 | 2/2007 | Sieracki et al. |

(56) References Cited

U.S. PATENT DOCUMENTS

| | | |
|---|---|---|
| 7,184,837 B2 | 2/2007 | Goetz |
| 7,191,014 B2 | 3/2007 | Kobayashi et al. |
| 7,209,787 B2 | 4/2007 | DiLorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,282 B2 | 3/2008 | Sakanaka et al. |
| 7,346,382 B2 | 3/2008 | McIntyre et al. |
| 7,388,974 B2 | 6/2008 | Yanagita |
| 7,437,193 B2 | 10/2008 | Parramon et al. |
| 7,450,997 B1 | 11/2008 | Pianca et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,209,027 B2 | 6/2012 | Butson et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,326,433 B2 | 12/2012 | Blum et al. |
| 8,340,775 B1 * | 12/2012 | Cullen .................. G16H 40/63 607/59 |
| 8,364,278 B2 | 1/2013 | Pianca et al. |
| 8,391,985 B2 | 3/2013 | McDonald |
| 8,429,174 B2 | 4/2013 | Ramani et al. |
| 18,452,415 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,589,316 B2 | 11/2013 | Lujan et al. |
| 8,594,800 B2 | 11/2013 | Butson et al. |
| 8,606,360 B2 | 12/2013 | Butson et al. |
| 8,620,452 B2 | 12/2013 | King et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Blum et al. |
| 9,020,789 B2 | 4/2015 | Butson et al. |
| 9,050,470 B2 | 6/2015 | Carlton et al. |
| 9,072,905 B2 | 7/2015 | Kokones et al. |
| 9,248,272 B2 | 2/2016 | Romero |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezai |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |

(56) References Cited

U.S. PATENT DOCUMENTS

| | | |
|---|---|---|
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0076535 A1 | 3/2010 | Pianca et al. |
| 2010/0113959 A1 | 5/2010 | Pascual-Leone et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kaula et al. |
| 2010/0179562 A1 | 7/2010 | Linker et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Butson et al. |
| 2011/0066407 A1 | 3/2011 | Butson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0238129 A1 | 9/2011 | Moffitt |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |

(56) References Cited

U.S. PATENT DOCUMENTS

| | | |
|---|---|---|
| 2012/0316615 A1 | 12/2012 | Digiore et al. |
| 2012/0316619 A1 | 12/2012 | Goetz et al. |
| 2012/0330622 A1 | 12/2012 | Butson et al. |
| 2013/0039550 A1 | 2/2013 | Blum et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0289380 A1 | 10/2013 | Molnar et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0122379 A1 | 5/2014 | Moffitt et al. |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0134031 A1 | 5/2015 | Moffitt et al. |
| 2015/0151113 A1 | 6/2015 | Govea et al. |
| 2016/0001087 A1* | 1/2016 | Moffitt .............. A61N 1/36175 607/60 |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0074662 A1* | 3/2016 | Moffitt .............. A61N 1/36125 607/72 |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0228692 A1 | 8/2016 | Steinke et al. |
| 2016/0256693 A1 | 9/2016 | Parramon |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0106197 A1 | 4/2017 | Wechter et al. |
| 2017/0252570 A1 | 9/2017 | Serrano Carmona et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Butson et al.. "Current Steering to control the volume of tissue activated during deep brain stimulation," vol. 1, No. 1, Dec. 3, 2007. pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Remus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zone incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45 (6). (Jun. 1998),766-772.

Rose, T. L., "Electrical stimulation with Pt electrodes. VIII. Electrochemically safe charge injection limits with 0.2 ms pulses [neuronal application]", IEEE Transactions on Biomedical Engineering, 37(11 ), (Nov. 1990), 1118-1120.

Rubinstein, J. T., et al., "Signal coding in cochlear implants: exploiting stochastic effects of electrical stimulations", Ann Otol Laryngol Suppl.. 191, (Sep. 2003), 14-9.

Schwan, H.P., et al., "The conductivity of living tissues.", Ann NY Acad Sci., 65(6). (Aug. 1957), 1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

(56) References Cited

OTHER PUBLICATIONS

Siegel, Ralph M. et al., "Spatiotemporal dynamics of the functional architecture for gain fields in inferior partial lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 2005),251-65.
Vidailhet, M., et al., "Bilateral deep-brain stimulation of the globus pallidus in primary generalized dystonia", N Engl J Med. 352(5) (Feb. 3, 2005),459-67.
Izad, Oliver, "Computationally Efficient Department in Predicating Axonal Excitation," Dissertation for Master Degree, Department of Biomedical Engineering, Case Western Reserve University, May 2009.
Jaccard, Paul, "Elude comparative de la distribution florate dans une portion odes Aples et des Jura," Bulletin de la Societe Vaudoise des Sciences Naturelles (1901), 37:547-579.
Dice, Lee R., "Measures of the Amount of Ecologic Association Between Species," Ecology 26(3) (1945): 297-302. doi:10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/BF01908075.
Cover. T.M. et al., "Elements of information theory," (1991) John Wiley & Sons, New York, NY.
Meila, Marina, "Comparing Clusterings by the Variation of Information," Learning Theory and Kernel Machines (2003) 173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No, 1, pp. 1-8.
Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode. Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J. , et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004), 719-28.
Wei, X. F., et al., "Current density distributions, field distributions and impedance analysis of segmented deep brain stimulation electrodes", J Neural Eng .. 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.)
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4), (Jul.-Aug. 1995), 375-385.
Miocinovic, S., et al., "Sensitivity of temporal excitation properties to the neurol element activated by extracellualr stimulation", J Neurosci Methods. 132(1), (Jan. 15, 2004), 91-9.
Hunka. K. et al., Nursing Time to Program and Assess Deep Brain Stimulators in Movement Disorder Patients, J. Neursci Nurs., 37: 204-10 (Aug.2005).
Moss, J. , et al., "Electron microscopy of tissue adherent to explanted electrodes in dystonia and Parkinson's disease", Brain, 127{Pt 12). (Dec. 2004),2755-63.
Montgomery, E. B., et al., "Mechanisms of Deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Envoromemt", htt12:// www.sci.utah.edu/cibc/software/index.html, MCRR Center for Intergrative Biomedical Computing,(2004).
Andrews, R.J., "Neoroprotection trek—the next generation: neuromodulation I. Techniques—deep brain stimulation, vagus nerve stimulation, and transcranial magnetic stimulation.", Ann NY Acad Sci. 993. (May 2003),1-13.
Carnevale, N.T. et al., "The Neuron Book," Cambridge, UK: Cambridge University Press (2006), 480 pages.
Chaturvedi: "Developmental of Accurate Computational Models for Patient-specific Deep Brain Stimulations," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elesvier, Amsterdam, NL, vol. 3, No. 2 Apr. 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.

(56) References Cited

OTHER PUBLICATIONS

Brown, J. "Motor Cortex Stimulation,"Neurosurgical Focus ( Sep. 15, 2011) 11(3):E5.
Budai et al., "Endogenous Opiod Peptides Acting at m-Opioid Receptors in the Dorsal Hom contribute to Midbrain Modulation of Spinal Nociceptive Nerouns," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular field potentials and the frequency-filtering properties of extracellular space", Biophys J .. 86(3). (Mar. 2004),1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977), 440-443.
Butson, Christopher R., et al., "Deep Brain Stimulaiton of the Subthalamic Nucleus: Model-Based Analysis of the Effects of Electrode Capacitance on the Volume of Activation", Proceedings of the 2nd International IEEE EMBS, (Mar. 16-19, 2005), 196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assited Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp, 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson, Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al,, "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1591-1604.
Mcintyre, C. C., et al., "Microstimulation of spinal motoneurons: a model study," Proceedings of the 19th Annual International Conference of the IEEE Engineering in Medice and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system., Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aferpotentials on the recovery cycle," J Neurophysiol, 87(2) (Feb. 2002), pp. 995-1006.
Mcintyre, Cameron C., et al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern., 79(1) (Jul. 1998), pp. 29-37.
Mcintyre, Cameron C., et al., "Uncovering the mechanism(s) of action of deep brain stimulation: activation, inhibition, or both," 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.

(56) References Cited

OTHER PUBLICATIONS

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59(5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulaiton," Neurology, 60(5) (Mar. 11, 2003), pp. 786-790.

Pierpaoli, C., et al., "Toward a quantitative assessment of diffusion anisotropy," Magn Reson Med., 36(3) (Dec. 1996), pp. 893-906.

Plonsey, R., et al., "Considerations of quasi-stationarity in electrophysiological systems," Bull Math Biophys., 29(4) (Dec. 1967), pp. 657-664.

Ranck, J B., "Specific impedance of rabbit cerebral cortex," Exp. Neural., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous systems: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neural. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A. et al., "In Electroanesthesia: Biomedical and Biophysical Studies," A Sances and SJ Larson, Eds., Academic Press, NY (1975), pp. 114-124.

Si. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus," Neural Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001 ), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Wakana, S., et al., "Fiber tract-based atlas of human white matter anatomy," Radiology, 230(1) (Jan. 2004), pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.

Yianni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantable Microstimulators" ICM '98 Proceedings of the Tenth International Conference, pp. 67-70.

Butson, Christopher R., et al., "Patient-specific analysis stimulation of the volume of tissue activated during deep brain stimulation", NeuroImage. vol. 34. vol.(2007),661-670.

Adler, DE., et al., "The tentorial notch: anatomical variation, morphometric analysis, and classification in 100 human autopsy cases," J. Neurosurg., 96(6), (Jun. 2002), pp. 1103-1112.

Jones et al., "An Advanced Demultiplexing System for Physiological Stimulation", IEEE Transactions on Biomedical Engineering, vol. 44 No. Dec. 12, 1997, pp. 1210-1220.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

(56) References Cited

OTHER PUBLICATIONS

Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R, et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (lhalamotoy and stimulation) stereotactic surgery of the VIM thalamic nucleus for bilateral Parkinson disease," Appl Neurophysiol, vol. 50, (1987), pp. 344-346.
Benabid, AL., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science, (LNCS), vol. 4191, pp. 429-437, LNCS, Springer, Berlin, DE.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg, Focus; 15(1) (Jul. 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention-Part 11, Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol, 4681 Medical Imaging 2002: Visualization, Image-Guided Procedures, and Display (May 2002), pp. 184-195.

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434

(56) References Cited

OTHER PUBLICATIONS

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.

Andrade-Souza, "Comparison of Three Methods of Targeting the Subthalamic Nucleus for Chronic Stimulation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008.

Buston et al., "Tissue and Electrode Capacitance Reduce Neural Activation Volumes During Deep Brain Stimulation" Clinical Neurophysiology, 116:2490-2500, Oct. 2005.

Butson et al., "Source and Effects of Electrode Impedance During Deep Brain Stimulation", Clinical Neurophysiology, 117:44 7-454, Dec. 2005.

D'Haese et al., "Computer-Aided Placement of Deep Brain Stimulators: From Planning to Intraoperative Guidance", IEEE Transaction on Medical Imaging, 24:1469-1478, Nov. 2005.

Gross et al., "Electrophysiological Mapping for the Implantation of Deep Brain Stimulators for Parkinson's Disease and Tremor", Movement Disorders, 21 :S259-S283, Jun. 2006.

Halpern et al., "Brain Shift During Deep Brain Stimulation Surgery for Parkinson's Disease", Stereotact Funct. Neurosurg., 86:37-43, published online Sep. 2007.

Herzog et al., "Most Effective Stimulation Site in Subthalamic Deep Brain Stimulation for Parkinson's Disease", Movement Disorders, 19:1050-1099, on line Mar. 2004.

Jeon et al., A Feasibility Study of Optical Coherence Tomography for Guiding Deep Brain Probes, Journal of Neuroscience Methods, 154:96-101, Jun. 2006.

Khan et al., "Assessment of Brain Shift Related to Deep Brain Stimulation Surgery", Sterreotact Funct. Neurosurg., 86:44-53, published online Sep. 2007.

Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

Machado et al., "Deep Brain Stimulation for Parkinson's Disease: Surgical Technique and Perioperative Management", Movement Disorders, 21 :S247-S258, Jun. 2006.

Maks et al., "Deep Brain Stimulation Activation Volumes And Their Association with Neurophysiological Mapping and Therapeutic Outcomes", Downloaded from jnnp.bmj.com, pp. 1-21, published online Apr. 2008.

Moran et al., "Real-Time Refinment of Subthalamic Nucleous Targeting Using Bayesian Decision-Making on the Root Mean Square Measure", Movement Disorders, 21: 1425-1431, published online Jun. 2006.

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural Neurosurg. Psychiatry, 76:1161-1163. Aug. 2005

Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Butson, Christopher R., et al., "Sources and effects of electrode impedance during deep brain stimulation", Clinical Neurophysiology. vol. 117.(2006),447-454.

An, et al., "Prefronlal cortical projections to longitudinal columns in the midbrain periaqueductal gray in macaque monkeys," J Comp Neural 401 (4) (1998), pp. 455-479.

Bulson, C. R., et al., "Tissue and electrode capacitance reduce neural activation volumes during deep brain stimulation," Clinical Neurophysiology, vol. 116 (2005), pp. 2490-2500.

Carmichael, S. T., et al., "Connectional networks within the orbital and medial prefronlal cortex of macaque monkeys," J Comp Neural 371 (2) (1996), pp. 179-207.

Croxson, et al., "Quantitative investigation of connections of the prefronlal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman et al., "Deep brain stimulation for inractable obsessive compulsive disorder: pilot study using a blinded, staggered-onset design," Biol Psychiatry 67 (6) (2010), pp. 535-542.

Greenberg, et al., "Deep brain stimulation of the ventral capsile/ventral striatum for obsessive-compilsive disorder: wroldwide experience," Mol Psychiatry 15 (1) (2010), pp. 64-79.

Greenberg. et al., "Three-year outcomes in deep brain stimulation for highly resistant obsessive-compulsive disorder," Neuropsychopharmacology 31 (11) (2006), pp. 2384-2393.

Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

(56) References Cited

OTHER PUBLICATIONS

Lujan, J.L. et al., "Automated 3-Dimensional Brain Atlas Fitting to Microelectrode Recordings from Deep Brain Stimulation Surgeries," Stereotact. Funel. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre, C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
McIntyre, Cameron, et al., "Finite elements analysis of the current-density and electric field generated by metal microelctrodes", Ann Biomed Eng . 29(3), (2001 ),227-235.
Foster, K. R., et al., "Dielectric properties of tisssues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med .. 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation. Engineering (2005), 160-165.
Holsheimer, J., et al., "Chronaxie calculated from current-duration and voltage-duration data", J Neurosci Methods. 97(1). (Apr. 1, 2000),45-50.
Hines, M.L., et al., "The NEURON simulation enviroment", Neural Comput. 9(6). (Aug. 15, 1997), 1179-209.
Hezog, J., et al., "Most effective stimulation site in subthalamic deep brain stimulation for Parkinson's disease", Mov Disord. 19(9). (Sep. 2004), 1050-4.
Hershey, T., et al., "Cortial and subcortial blood flow effects of subthalamic nucleus stimulation in PD.", Neurology 61(6). (Sep. 23, 2003),816-21.
Hemm, S., et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: sterotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EGG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T., et al., "Stimulation of the subthalamic nucleus changes the firing pattern of pallidal neurons", J Neurosci. 23(5). (Mar. 1, 2003).1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
McNaughtan et al., "Electrochemical Issues in Impendance Tomgraphy", 1st World Congress on Industrial Process Tomography, Buxton, Greater Manchester, Apr. 14-17, 1999.
Grill, WM., et al., "electrical properties of implant encapsulation tissue", Ann Biomed Eng. vol. 22 (1994),23-33.
Grill, W. M., "Deep brain stimulation creates an informational lesion of the stimulated nucleus", Neuroreport. 15I7t (May 19, 2004), 1137-40.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.
International Search Report and Written Opinion for PCT/US2018044426 dated Oct. 4, 2018.

\* cited by examiner

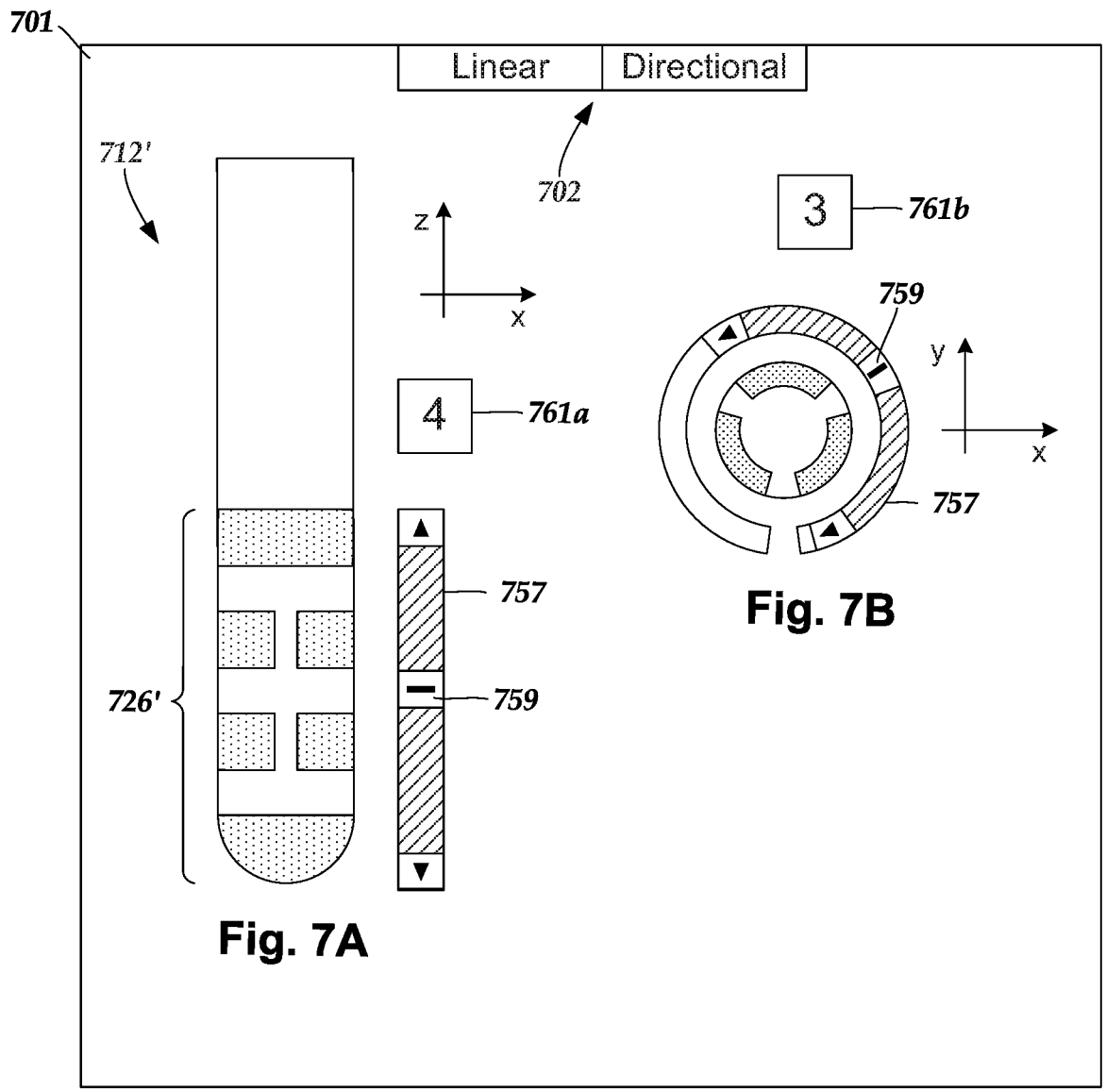
Fig. 7A
Fig. 7B
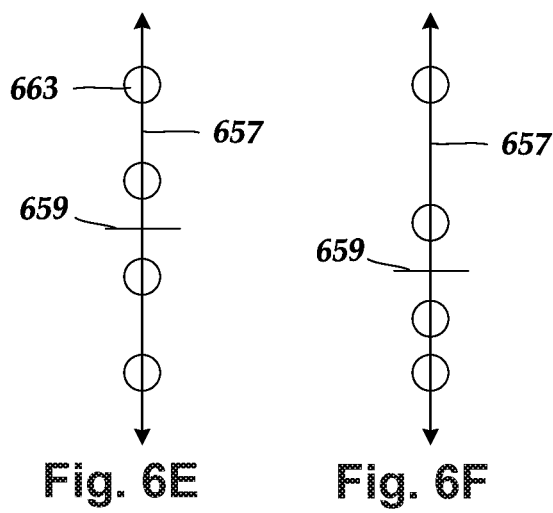
Fig. 6E  Fig. 6F

SYSTEMS AND METHODS FOR CONTROLLING ELECTRICAL STIMULATION USING MULTIPLE STIMULATION FIELDS

CROSS-REFERENCE TO RELATED APPLICATIONS

This application claims the benefit under 35 U.S.C. § 119(e) of U.S. Provisional Patent Application Ser. No. 62/545,855, filed Aug. 15, 2017, which is incorporated herein by reference.

FIELD

The present invention is directed to the area of electrical stimulation systems and methods of using the systems. The present invention is also directed to systems and methods for enabling a user to control electrical stimulation using multiple stimulation fields.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include an implantable pulse generator ("IPG"), one or more leads, and an array of stimulator electrodes on each lead. The stimulator electrodes are in contact with or near the nerves, muscles, or other tissue to be stimulated. The pulse generator generates electrical pulses that are delivered by the electrodes to body tissue.

BRIEF SUMMARY

In one embodiment, a system for programming electrical stimulation by an electrical stimulation lead includes a display and a processor coupled to the display. The processor is configured to present an interface on the display including user-selectable controls to define stimulation fields and repeating stimulation patterns for delivering the stimulation fields temporally-coordinated with each other. The user-selectable controls include a field control to define the number of stimulation fields, at least one location control to define locations of the stimulation fields relative to the electrical stimulation lead, at least one repetition control to define a repetition frequency of the stimulation pattern, and at least one temporal-adjustment control to define a temporal adjustment of at least one of the stimulation fields relative to another one of the stimulation fields. The processor is further configured to receive selections of the user-selectable controls to define the stimulation fields and the repeating stimulation patterns; and initiate a signal that provides a pulse generator with instructions that enable the pulse generator to generate the stimulation fields according to the repeating stimulation pattern using the electrical stimulation lead coupled to the pulse generator.

In at least some embodiments, for each of the stimulation fields, the repeating stimulation patterns include a first time-interval over which a series of pulses having a set of stimulation parameters are emitted and a nonoverlapping second time-interval over which no pulses are emitted, the first time-interval and the second time-interval collectively forming a stimulation-pattern time interval. In at least some embodiments, for each of the stimulation fields, the stimulation-pattern time intervals are the same length. In at least some embodiments, for each of the stimulation fields, the first time-intervals are the same length. In at least some embodiments, for each of the stimulation fields, the second time-intervals are the same length. In at least some embodiments, for each of the stimulation fields, the first time-interval occurs while each of the remaining stimulation fields are in their respective second time intervals.

In at least some embodiments, the at least one temporal-adjustment control enables adjustment of the time duration of the stimulation-pattern time interval for each stimulation field of the stimulation fields. In at least some embodiments, the at least one temporal-adjustment control enables adjustment of the first time-interval length for each stimulation field of the stimulation fields.

In at least some embodiments, the stimulation fields include a first stimulation field and a second stimulation field, where the stimulation-pattern time interval includes an inter-pulse time delay between an end of the first time-interval of the first stimulation field and a beginning of the first time-interval of the second stimulation field. In at least some embodiments, the at least one temporal-adjustment control enables adjustment of a time-interval length of the inter-pulse time delay.

In at least some embodiments, the interface includes a graphical representation of each of the stimulation fields arranged into a set of repeating time blocks of equal duration to one another, where each time block of the set of repeating time blocks has a time duration that is equal to the stimulation-pattern time interval, and where, for each of the stimulation fields, each time block includes a single first time-interval. In at least some embodiments, the interface includes a user-selectable control for selecting, for each time block of the set of repeating time blocks, whether or not each stimulation field of the stimulation fields is stimulating patient tissue. In at least some embodiments, the interface includes a user-selectable control for selecting, for increments of time greater than a time block of the set of repeating time blocks, whether or not each stimulation field of the stimulation fields is stimulating patient tissue.

In at least some embodiments, the at least one temporal-adjustment control enables adjustment of a temporal-offset between repeating stimulation patterns of a first stimulation field of the stimulation fields from the repeating stimulation patterns of the remaining stimulation fields.

In at least some embodiments, the interface further includes a user-selectable control for selecting pulse frequencies for the series of pulses emitted over the first time-interval.

In at least some embodiments, the at least one location control enables selection of a subset of the electrodes for generating the stimulation fields. In at least some embodiments, the at least one location control enables selection of a field center for the selected subset of the electrodes for generating the stimulation fields. In at least some embodiments, the at least one location control enables selection of locations of the stimulation fields relative to the electrical stimulation lead both linearly and circumferentially with respect to the electrical stimulation lead.

In at least some embodiments, the electrical stimulation system further includes a lead configured and arranged for implantation into a patient, the lead including a lead body having a proximal portion and a distal portion; and electrodes disposed along the distal portion of the lead body. In at least some embodiments, the electrical stimulation system further includes a pulse generator coupleable to the lead, the pulse generator configured and arranged for providing electrical stimulation signals to the electrodes for stimulation of patient tissue.

In another embodiment, a non-transitory computer-readable medium has processor-executable instructions for programming electrical stimulation by an electrical stimulation lead. The processor-executable instructions, when installed onto a device, enable the device to perform actions, including presenting an interface on a coupled display. The interface includes user-selectable controls to define stimulation fields for the electrical stimulation lead and repeating stimulation patterns for delivering the stimulation fields temporally-coordinated with each other. The user-selectable controls include a field control to define the number of stimulation fields, at least one location control to define locations of the stimulation fields relative to the electrical stimulation lead, at least one repetition control to define a repetition frequency of the repeating stimulation patterns, and at least one temporal-adjustment control to define a temporal adjustment of at least one of the stimulation fields from another one of the stimulation fields. The processor-executable instructions, when installed onto a device, enable the device to perform further actions, including receiving selections of the user-selectable controls to define the stimulation fields and the repeating stimulation patterns; and initiating a signal that provides a pulse generator with instructions that enable the pulse generator to generate the stimulation fields according to the repeating stimulation patterns using the electrical stimulation lead coupled to the pulse generator.

In yet another embodiment, a method for providing electrical stimulation using multiple stimulation fields, with each of the stimulation fields emitting repeating stimulation patterns, includes advancing an electrical stimulation lead to a target parenchymal population within the patient, the electrical stimulation lead including electrodes; coupling the electrical stimulation lead to a pulse generator configured and arranged for providing electrical stimulation signals to the electrodes for stimulation of patient tissue; and using the electrical stimulation system described above for initiating a signal that provides the pulse generator with instructions that enable the pulse generator to generate the stimulation fields using the electrical stimulation lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIGS. 6E-6F is a schematic view of one embodiment of several different field centers obtainable from the electrodes of the graphical representations of the leads of the displays of FIGS. 6A-6D, according to the invention;

FIG. 7A is a schematic side view of one embodiment of a display showing a graphical representation of a lead with segmented electrodes disposed thereon, and user-selectable controls for selecting and adjusting one or more fields obtainable from the segmented electrodes, according to the invention;

FIG. 7B is a schematic side view of a second embodiment of the display of FIG. 7A, according to the invention;

DETAILED DESCRIPTION

The present invention is directed to the area of electrical stimulation systems and methods of using the systems. The present invention is also directed to systems and methods for enabling a user to control electrical stimulation using multiple stimulation fields.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
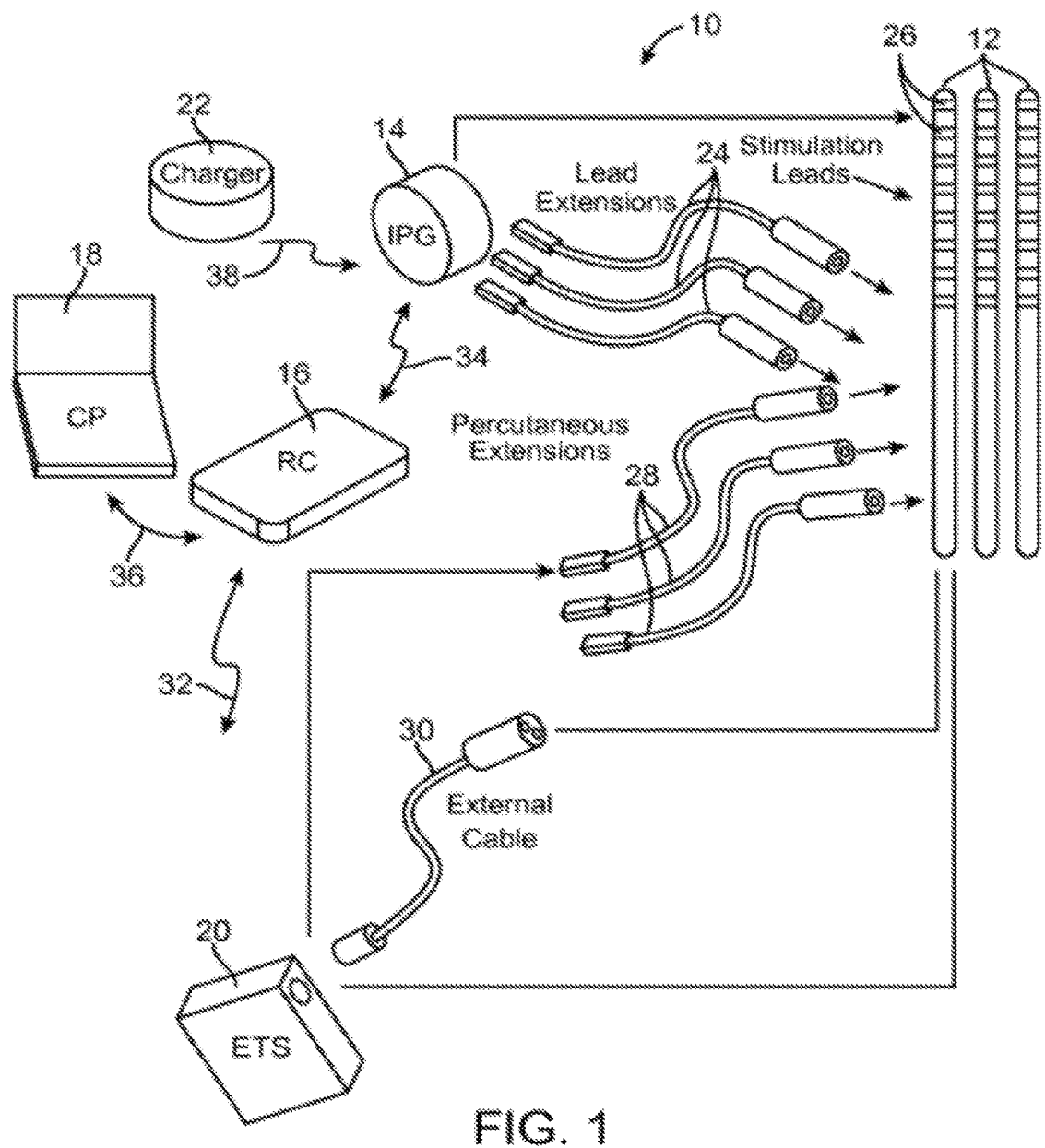
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
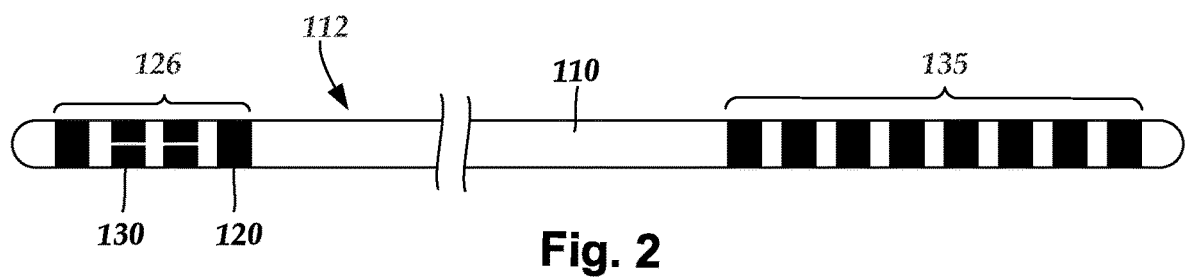
FIG. 2 is a schematic side view of one embodiment of an electrical stimulation lead, according to the invention.

FIG. 2 illustrates one embodiment of a lead 112 with electrodes 126 disposed at least partially about a circumference of the lead 112 along a distal end portion of the lead and terminals 135 disposed along a proximal end portion of the lead. The lead 112 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 112 can be inserted into the cranium and brain tissue with the assistance of a stylet (not shown). The lead 112 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 112, advance the lead 112, retract the lead 112, or rotate the lead 112.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 112 for deep brain stimulation can include stimulation electrodes, recording electrodes, or both. In at least some embodiments, the lead 112 is rotatable so that the stimulation electrodes can be aligned with the target neurons after the neurons have been located using the recording electrodes.

Stimulation electrodes may be disposed on the circumference of the lead 112 to stimulate the target neurons. Stimulation electrodes may be ring-shaped so that current projects from each electrode equally in every direction from the position of the electrode along a length of the lead 112. In the embodiment of FIG. 2, two of the electrodes 126 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 112 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 112 has a cross-sectional diameter of no more than 1.5 mm and may be in the range of 0.5 to 1.5 mm. In at least some embodiments, the lead 100 has a length of at least 10 cm and the length of the lead 112 may be in the range of 10 to 70 cm.

The electrodes 126 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference. Segmented electrodes can also be used for other stimulation techniques including, but not limited to, spinal cord stimulation, peripheral nerve stimulation, dorsal root ganglion stimulation, or stimulation of other nerves, muscles, and tissues.

Figure 3:
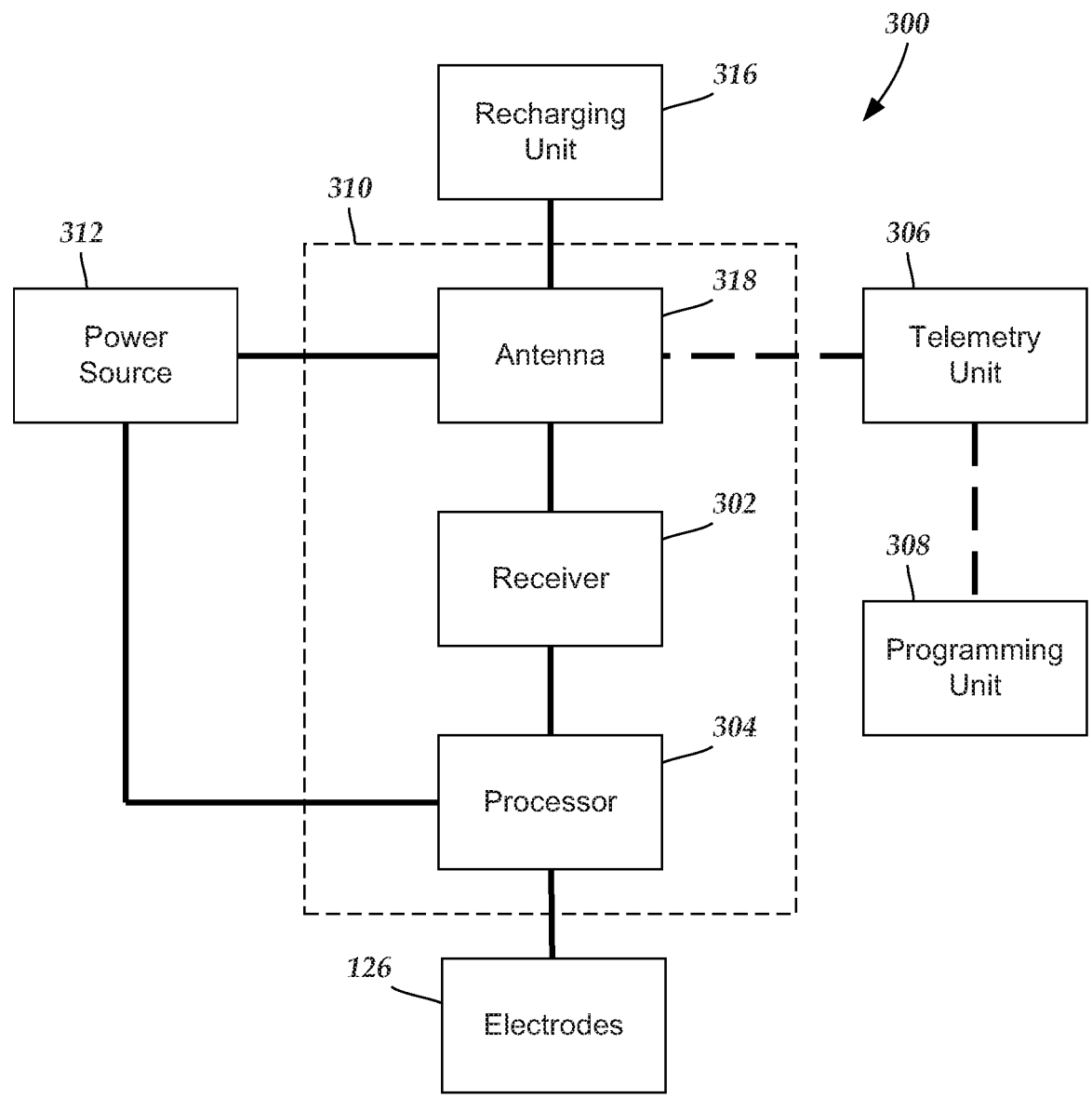
FIG. 3 is a schematic overview of one embodiment of components of a stimulation system, including an electronic subassembly disposed within a control module, according to the invention.

FIG. 3 is a schematic overview of one embodiment of components of an electrical stimulation system 300 including an electronic subassembly 310. It will be understood that the electrical stimulation system can include more, fewer, or different components and can have a variety of different configurations including those configurations disclosed in the stimulator references cited herein.

Some of the components (for example, a power source 312, an antenna 318, a receiver 302, and a processor 304) of the electrical stimulation system can be positioned on one or more circuit boards or similar carriers within a sealed housing of an implantable pulse generator (see e.g., 14 in FIG. 1), if desired. Any power source 312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 318 or a secondary antenna. The external power source can be in a device that is mounted on the skin of the user or in a unit that is provided near the user on a permanent or periodic basis.

If the power source 312 is a rechargeable battery, the battery may be recharged using the optional antenna 318, if desired. Power can be provided to the battery for recharging by inductively coupling the battery through the antenna to a recharging unit 316 external to the user. Examples of such arrangements can be found in the references identified above.

Figure 4:
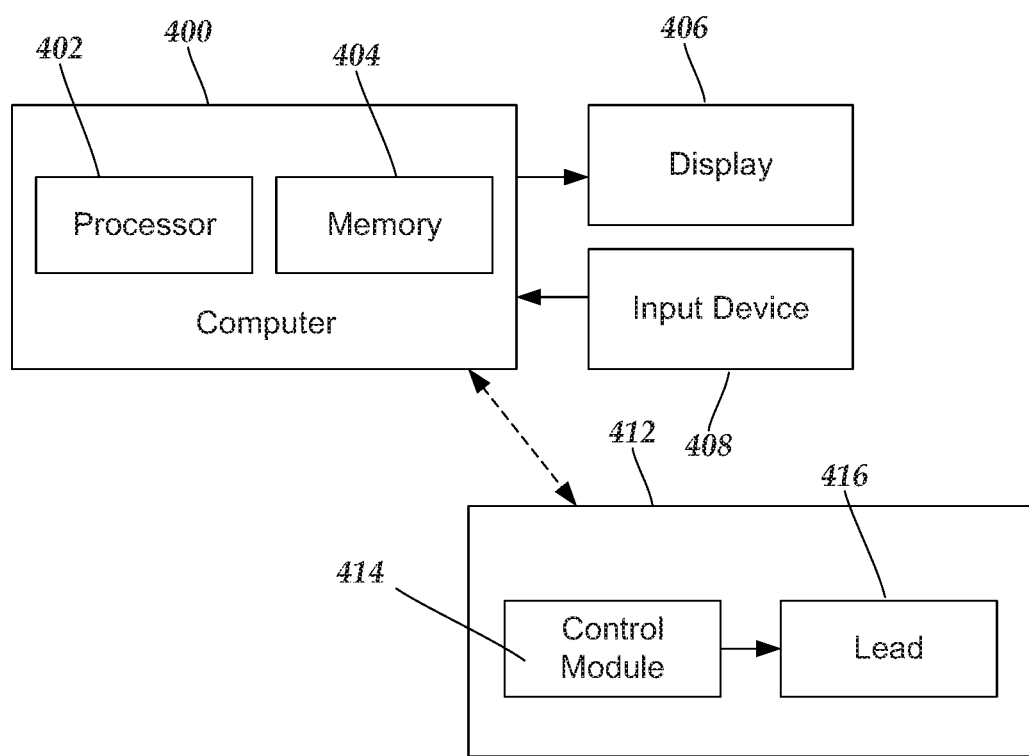
FIG. 4 is a schematic illustration of one embodiment of a system for practicing the invention.

The electronic subassembly 310 and, optionally, the power source 312 can be disposed within a control module (e.g., the IPG 14 or the ETS 20 of FIG. 1). The control module is shown in FIG. 4.

In one embodiment, electrical stimulation signals are emitted by the electrodes 126 on the paddle or lead body to stimulate nerve fibers, muscle fibers, or other body tissues near the electrical stimulation system. The processor 304 is generally included to control the timing and electrical characteristics of the electrical stimulation system. For example, the processor 304 can, if desired, control one or more of the timing, frequency, strength, duration, and waveform of the pulses. In addition, the processor 304 can select which electrodes can be used to provide stimulation, if desired. In some embodiments, the processor 304 selects which electrode(s) are cathodes and which electrode(s) are anodes. In some embodiments, the processor 304 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 308 that, for example, allows modification of pulse characteristics. In the illustrated embodiment, the processor 304 is coupled to a receiver 302 which, in turn, is coupled to the optional antenna 318. This allows the processor 304 to receive instructions from an external source to, for example, direct the pulse characteristics and the selection of electrodes, if desired.

In one embodiment, the antenna 318 is capable of receiving signals (e.g., RF signals) from an external telemetry unit 306 which is programmed by the programming unit 308. The programming unit 308 can be external to, or part of, the telemetry unit 306. The telemetry unit 306 can be a device that is worn on the skin of the user or can be carried by the user and can have a form similar to a pager, cellular phone, or remote control, if desired. As another alternative, the telemetry unit 306 may not be worn or carried by the user but may only be available at a home station or at a clinician's office. The programming unit 308 can be any unit that can provide information to the telemetry unit 306 for transmission to the electrical stimulation system 300. The programming unit 308 can be part of the telemetry unit 306 or can provide signals or information to the telemetry unit 306 via a wireless or wired connection. One example of a suitable programming unit is a computer operated by the user or clinician to send signals to the telemetry unit 306.

The signals sent to the processor 304 via the antenna 318 and the receiver 302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 300 to cease operation, to start operation, to start charging the battery, or to stop charging the battery. In other embodiments, the stimulation system does not include the antenna 318 or receiver 302 and the processor 304 operates as programmed.

Optionally, the electrical stimulation system 300 may include a transmitter (not shown) coupled to the processor 304 and the antenna 318 for transmitting signals back to the telemetry unit 306 or another unit capable of receiving the signals. For example, the electrical stimulation system 300 may transmit signals indicating whether the electrical stimulation system 300 is operating properly or not or indicating when the battery needs to be charged or the level of charge remaining in the battery. The processor 304 may also be capable of transmitting information about the pulse characteristics so that a user or clinician can determine or verify the characteristics.

FIG. 4 illustrates one embodiment of a system for practicing the invention. The system can include a computer 400 or any other similar device that includes a processor 402 and a memory 404, a display 406, an input device 408, and, optionally, the electrical stimulation system 412.

The computer 400 can be a laptop computer, desktop computer, tablet, mobile device, smartphone or other devices that can run applications or programs, or any other suitable device for processing information and for presenting a user interface. The computer can be, for example, a clinician programmer, patient programmer, or remote programmer for the electrical stimulation system 412. The computer 400 can be local to the user or can include components that are non-local to the user including one or both of the processor 402 or memory 404 (or portions thereof). For example, in some embodiments, the user may operate a terminal that is connected to a non-local computer. In other embodiments, the memory can be non-local to the user.

The computer 400 can utilize any suitable processor 402 including one or more hardware processors that may be local to the user or non-local to the user or other components of the computer. The processor 402 is configured to execute instructions provided to the processor, as described below.

Any suitable memory 404 can be used for the processor 402. The memory 404 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 406 can be any suitable display device, such as a monitor, screen, display, or the like, and can include a printer. The input device 408 can be, for example, a keyboard, mouse, touch screen, track ball, joystick, voice recognition system, or any combination thereof, or the like and can be used by the user to interact with a user interface or clinical effects map.

The electrical stimulation system 412 can include, for example, a control module 414 (for example, an implantable pulse generator) and a lead 416 (for example, the lead illustrated in FIG. 1.) The electrical stimulation system 412 may communicate with the computer 400 through a wired or wireless connection or, alternatively or additionally, a user can provide information between the electrical stimulation system 412 and the computer 400 using a computer-readable medium or by some other mechanism. In some embodiments, the computer 400 may include part of the electrical stimulation system.

In at least some instances, a treating physician may wish to tailor the stimulation parameters (such as which one or more of the stimulating electrode contacts to use, the stimulation pulse amplitude (such as current or voltage amplitude depending on the stimulator being used,) the stimulation pulse width, the stimulation frequency, or the like or any combination thereof) for a particular patient to improve the effectiveness of the therapy. Electrical stimulation systems can provide a user interface that facilitates parameter selections. Examples of such systems and interfaces can be found in, for example, U.S. Pat. Nos. 8,326,433; 8,831,731; 8,849,632; 9,050,470; and 9,072,905; and U.S. Patent Application Publication No. 2014/0277284, all of which are incorporated herein by reference in their entireties.

Figure 5A:
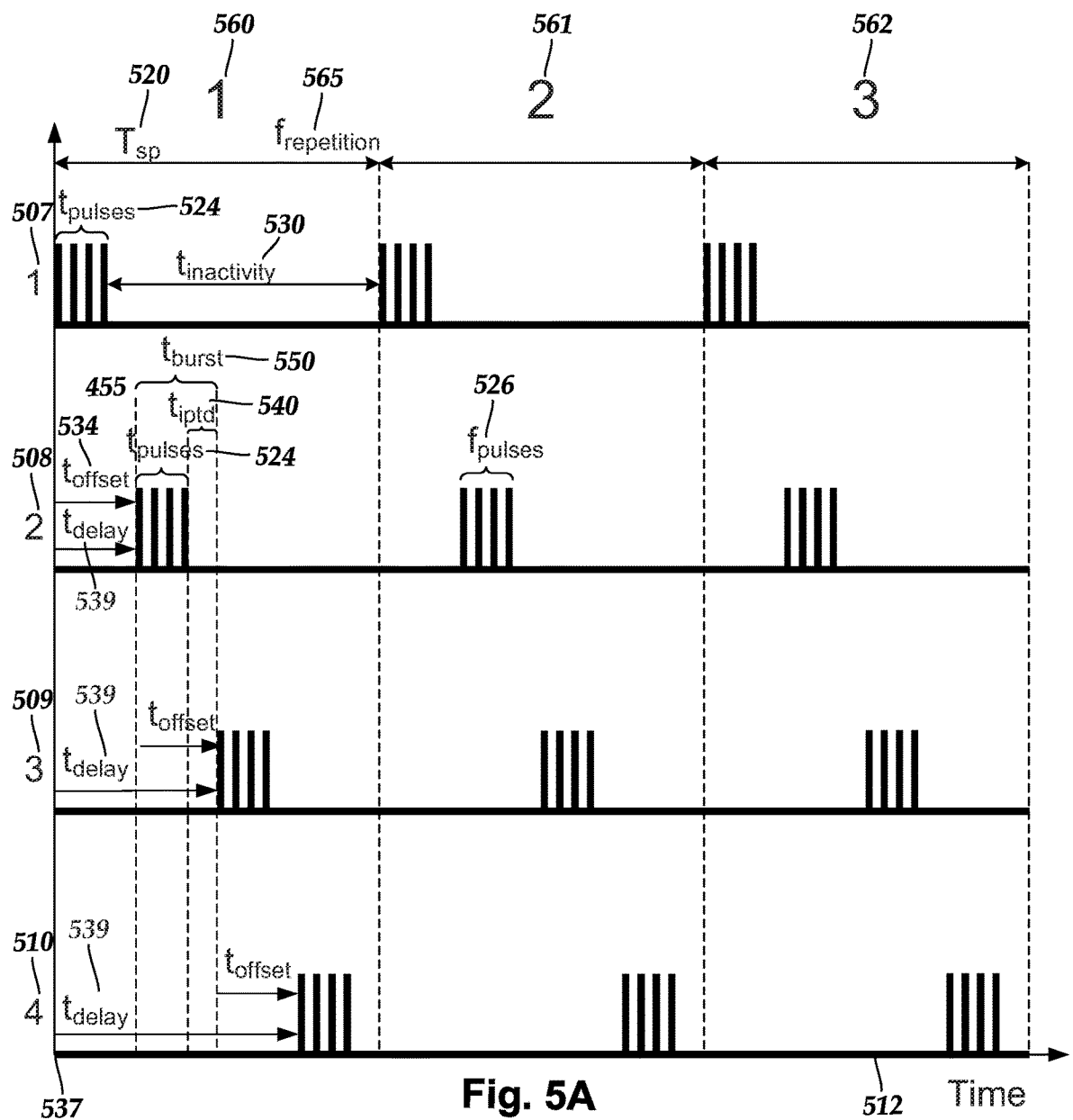
FIG. 5A is a schematic view of one embodiment of a series of repeating stimulation patterns generated by four different stimulation fields over a period of time, according to the invention.

Turning to FIG. 5A, conventional stimulation may involve generating a single stimulation field for each lead, such that all electrical pulses emitted from the lead do so at the same time. The stimulation field is typically generated to stimulate as many targeted neurons as feasible, while also avoiding stimulation of as many untargeted neurons as feasible.

At least some neurological conditions (e.g., Parkinsonism, essential tremor, dystonia, or the like) involve populations of neurons in the brain that become overactive. Such over-activity may involve pathological synchronous firings of action potentials along affected parenchymal populations.

Although the invention is not limited to any particular theory, it is thought that electrical stimulation can be used to desynchronize action potential firings along at least some neurons of the affected neuron population. For example, asynchronous stimulation can be used to produce a coordinated reset of synchronous action potential firings.

One way to provide asynchronous stimulation is to stimulate neurons using multiple stimulation fields. In some instances, the electrodes of one or more leads are used to generate a series of stimulation fields ("fields"), where each field is generated by a different subset of electrodes (although the subsets may be overlapping). Each field has a set of stimulation parameters (e.g., frequency, pulse width, and the like). The stimulation parameters for each field can be either the same or different from the remaining fields. In at least some embodiments, the period for two different stimulation fields are temporally offset from one another. The difference in stimulation timing may reduce, or even prevent, undesired neuronal synchronization. Each field stimulates different subpopulations of neurons with or without temporal or physical overlap with one or more other fields.

The electrodes can either be in close physical proximity to one another, or physically spaced-apart from one another. The electrodes may be disposed along a single implanted lead, or along multiple implanted leads. When multiple leads are utilized, the multiple leads may be coupled to the same control module, or to separate control modules in communication with one another (to coordinate the stimulation timing or stimulation parameters). The electrodes may be implanted at the same target stimulation location or along two different target stimulation locations within the patient. In at least some embodiments, the two or more electrodes are implanted within the patient's brain.

It is thought, although not necessary to the invention, that the electrical stimulation signals generated by the two or more electrodes generate effective electric fields (e.g., electrical stimulation propagating from the electrodes sufficient to cause an excitatory effect on axons surrounding the electrodes) that function to reset the undesired neural activity in a coordinated manner.

The electrodes may employ the same stimulation parameters, or may have one or more different stimulation parameters. The size and shape of the effective electric fields generated by the electrodes is based on the set of stimulation parameters used to generate the stimulation. In at least some instances, the size and shape of the effective electric fields generated by the two or more electrodes (or sets of electrodes) at a given set of stimulation parameters can be estimated, using one or more computer models (e.g., Volume of Tissue Activated Model, Stimulation Field Model, or the like or combinations thereof). In at least some embodiments, the effective volume of an electric field can be based on the region of tissue that experiences a stimulating effect in response to the electric field. Outside this effective volume, the electric field may be too weak to stimulate the tissue. Although sub-threshold stimulation may also provide some effects, the computer models may facilitate selection of implantation locations, or facilitate selection of stimulation parameters, or both. Examples of methods for determining the volume of activation can be found in, for example, U.S. Pat. Nos. 7,346,282; 8,180,601; 8,209,027; 8,326,433; 8,589,316; 8,594,800; 8,606,360; 8,675,945; 8,831,731; 8,849,632; 8.958,615; 9.020,789; and U.S. Patent Application Publications Nos. 2009/0287272; 2009/0287273; 2012/0314924; 2013/0116744; 2014/0122379; 2015/0066111; and 2016/0030749, all of which are incorporated herein by reference.

In some embodiments, the electrodes generate effective electric fields that are temporally offset (e.g., time-delayed) from one another so that the effective electric fields are out of phase from one another. In at least some embodiments, the electrodes are situated such the effective electric fields generated by the electrodes stimulate different populations of neurons in communication with one another (e.g., different neurons along a particular neural pathway). Although not wishing to be bound by a particular theory, the offsetting of the effective electric fields generated by the electrodes may be such that the downstream neurons are in a refractory period while the upstream neurons are propagating action potentials. In which case, the action potentials may be unable to propagate from the upstream neurons to the downstream neurons. Accordingly, undesired synchronized neuronal activity may be disrupted.

Any suitable time delay may be implemented between the electrodes. In some embodiments, the time delay may be determined by testing and observation. In some embodiments, the time delay is determined based on the frequency of the undesired neural activity (e.g., an observed shifted theta-band frequency) to be desynchronized or disrupted.

When the generated effective electric fields are time-delayed from one another, in some embodiments it may be desirable for the different electric fields to have little or no physical overlap. This may facilitate coordination the resetting of the action potential propagation by stimulating different populations of cells that are in communication with one another. When there is substantial physical overlap of effective electric fields between the electrodes, the stimulation parameters of the electrodes may be varied from one another in order to preferentially target some neurons more than others.

It has been shown that some stimulation parameters may preferentially target some neurons more than others. At least some physical characteristics of neurons (e.g., axon diameters, the presence or absence of a myelin sheath, or the like) may affect whether or not those neurons are excited by an effective electric field having a particular set of stimulation parameters. Consequently, in at least some embodiments, the stimulation parameters of at least one of the generated effective electric fields is varied in response to one or more physical characteristics of the neurons along the overlapping portion of the generated effective electric fields (e.g., axon diameters, the presence or absence of a myelin sheath, or the like).

The different stimulation parameters may enable a first set of stimulation parameters of a first electrode (or set of electrodes) to stimulate a first set of target neurons and a second set of stimulation parameters of a second electrode (or set of electrodes) to stimulate a second set of target neurons. In some embodiments, the second set of target neurons is a subset of the first set of target neurons. In which case, one narrow example of a stimulation procedure may include only a portion of the overall population of neurons within an overlapping portion of the effective electric fields becoming excitable during stimulation by a first electrode (or set of electrodes) with a first set of stimulation parameters, while all (or nearly all) of the overall population of neurons within the overlapping portion of the effective electric fields becoming excitable during stimulation by a second electrode with a second set of stimulation parameters.

In other embodiments, the second set of target neurons is mutually exclusive of the first set of target neurons. In which case, one example of a stimulation procedure may include a first portion of the overall population of neurons within an overlapping portion of the effective electric fields becoming excitable during stimulation by a first electrode (or set of electrodes) with a first set of stimulation parameters, and a second portion (mutually exclusive of the first portion) of the overall population of neurons within the overlapping portion of the effective electric fields becoming excitable during stimulation by a second electrode (or set of electrodes) with a second set of stimulation parameters.

In at least some embodiments, stimulation can be timed between the two or more electrodes such that some neurons are in a refractory period while other neurons are propagating action potentials. In which case, at least some of the action potentials are unable to propagate along the entire length of the neural pathway. Accordingly, undesired neural activity may be disrupted through desynchronization.

FIG. 5A shows one example of a series of repeating stimulation patterns generated by multiple stimulation fields ("fields") over a period of time. The illustrated embodiment includes a graphical depiction of stimulation patterns from each of four different fields: Field 1 507, Field 2 508, Field 3 509, and Field 4 510 graphed over time 512. In the illustrated embodiment, each of the four fields is generated using the same stimulation parameters. In alternate embodiments, one or more of the fields is generated using different stimulation parameters than at least one other field.

The illustrated stimulation patterns, each field includes a repeating stimulation-pattern time interval ($T_{sp}$) 520, which includes a first time-interval ($t_{pulses}$) 524 over which a series of pulses are emitted at a particular frequency ($f_{pulses}$) 526, followed by a second time-interval ($t_{inactivity}$) 530 when no pulses are emitted (i.e., a period of inactivity). For each particular field, the stimulation pattern is temporally-adjusted from the remaining fields by a time interval such that the series of pulses for a particular field (i.e., the first time-interval) occurs during the periods of inactivity (i.e., the second time-interval) of each of the remaining fields. For example, in the illustrated embodiment the beginning of the series of pulses for Field 2 508 is temporally-adjusted from the beginning of the series of pulses for Field 1 507 by an amount of time ($t_{offset}$) 534. And during the first time-interval 524 for Field 1 507, each of Field 2 508, Field 3 509, and Field 4 510 are in the second time-interval 530.

From an initial temporal starting point 537, each of the fields is temporally-adjusted from the remaining fields by a period of time ($t_{delay}$) 539 that is a multiple of the amount of time ($t_{offset}$) 534. For example, Field 2 508 is temporally-adjusted from the beginning of the series of pulses for Field 1 507 by a ($t_{delay}$) 539 equal to ($t_{offset}$) 534, while Field 3 509 is temporally-adjusted from the beginning of the series of pulses for Field 1 507 by a ($t_{delay}$) 539 equal to two times ($t_{offset}$) 534, and Field 4 510 is temporally-adjusted from the beginning of the series of pulses for Field 1 507 by a ($t_{delay}$) 539 equal to three times ($t_{offset}$) 534.

The stimulation-pattern time intervals 520 can be either the same or different for each of the fields. The first time-interval 524 can be either the same or different for each of the fields. The second time-interval 530 can be either the same or different for each of the fields.

The second time-interval ($t_{inactivity}$) 530 can include an inter-pulse time delay between the end of a series of pulses from one field and the beginning of the series of pulses from the next most closely temporally-offset field. In the illustrated embodiment, the beginning of the series of pulses for Field 3 509 is offset from the end of the series of pulses for Field 2 508 by inter-pulse time delay ($t_{iptd}$) 540. In the illustrated embodiment, the time interval $t_{burst}$ 550 refers to the time interval over which the series of pulses occur ($t_{pulses}$) 524 plus the inter-pulse time delay ($t_{iptd}$) 540. In other words, $t_{burst} = t_{pulses} + t_{iptd}$, where $t_{iptd}$ is the time interval during a "burst" when the field is "inactive". In the illustrated embodiment, the period of time $t_{burst}$ 550 is shown as occurring from the beginning of a series of pulses from Field 2 508 to the beginning of a series of pulses from Field 3 509.

FIG. 5A shows the stimulation fields arranged into a set of repeating time blocks: Block 1 560, Block 2 561, Block 3 562. Each time block is of equal duration and has a time duration that is equal in length to the stimulation-pattern time intervals ($T_{sp}$) 520. Each time block includes a single series of pulses (i.e., a first time-interval 524) for each of the stimulation fields. The blocks occur at a repetition frequency ($f_{repetition}$) 565, which can be user-adjustable via the user interface (see e.g., 455 in FIG. 4).

Figure 5B:
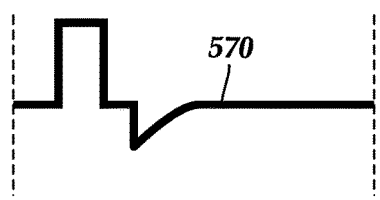
FIG. 5B is a schematic view of another embodiment of a portion of a stimulation pattern of FIG. 5A, according to the invention.

In FIG. 5A, each pulse of a given series of pulses is shown as a vertical line, or spike. The spikes shown FIG. 5A are idealized representations of pulses. Actual pulses may include more complex waveforms. FIG. 5B shows one embodiment of a possible waveform 570 suitable for use in lieu of any one of the spikes shown in FIG. 5A.

A user interface can be used to generate and control stimulation patterns. Certain rules can be applied to limit a range of user-selectable values, based on the stimulation patterns described in FIG. 5A. For example, the maximum time duration for $t_{burst}$ 550 is $T_{sp}$ 520/N, where N is the number of fields. Additionally, since $t_{burst}$ 550=$t_{pulses}$ 524+$t_{iptd}$ 540, $t_{iptd}$ 540 must be less than $T_{sp}$/N.

Figure 5C:
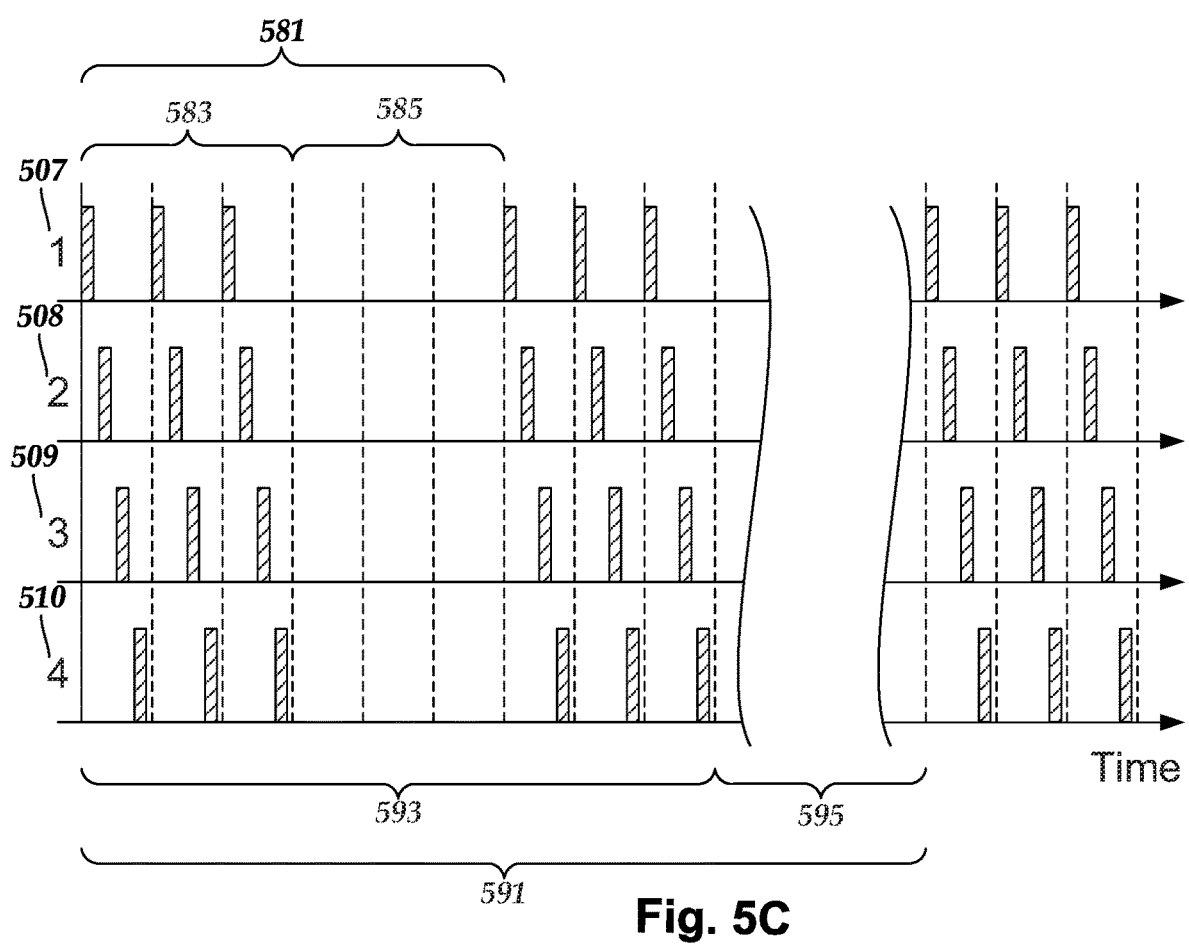
FIG. 5C is a schematic view of one embodiment of the series of repeating stimulation patterns of FIG. 5A depicted over a period of time that is longer than the period of time depicted in FIG. 5A, according to the invention.

Turning to FIG. 5C, the graphical depiction of repeating stimulation patterns (blocks) shown in FIG. 5A represents a portion of a "micro-schedule" of stimulation patterns. Micro-schedules, in turn, typically occur as part of a larger "macro-schedule" of stimulation patterns. Micro-schedules may, for example, define a particular stimulation session, while macro-schedules may define when stimulation sessions are to occur (e.g, once every fifteen minutes, once an hour, twice a day, three days a week, or the like).

FIG. 5C shows the series of repeating stimulation patterns of each of four different fields: Field 1 507, Field 2 508, Field 3 509, and Field 4 510 graphed over time 512. Note that in FIG. 5C, the first time-intervals (524 in FIG. 5A) over which a series of pulses are emitted are shown as cross-hatched rectangles instead of a series of spikes, for clarity of illustration.

In FIG. 5C, the stimulation patterns are shown over a period of time that is longer than the period of time depicted in FIG. 5A. A micro-schedule 581 includes at least one micro ON period of time 583 (represented in FIG. 5A as a repeating stimulation-pattern time interval ($T_{sp}$) 520, or a block), where stimulation occurs. A micro ON period of time 583 may be any suitable length of time, but is typically in the millisecond or second range of time. Typically, a stimulation session (described below) includes multiple repeating micro ON period of time 583 (e.g., stimulation-pattern time intervals). When multiple micro ON period of time 583 are used, each micro-schedule 581 also includes a micro OFF period of time 585 occurring after the micro ON period of time 583 until the last successive micro ON period of time 583 occurs. Stimulation does not occur during the micro OFF period of time 585. A macro-schedule 591 is a period of time that includes a stimulation session 593 followed by a macro OFF period of time 595 over which no stimulation occurs. A macro OFF period of time 595 can be any suitable length of time (e.g., minutes, hours, days, weeks, or the like)

In the embodiments shown in FIGS. 5A and 5C, Field 1 507, Field 2 508, Field 3 509, and Field 4 510 stimulate in the same order during each micro ON period of time 583. In at least some embodiments, the ordering of the stimulation occurring by different fields during micro ON periods of time 583 can be shuffled. Shuffling the order of stimulation may be beneficial to therapy. The ordering of the stimulation can be reshuffled at particular intervals of time (e.g., every block, after a particular number of milliseconds, after a particular number of seconds, or the like). As described below, a user interface can include one or more controls for activating a field shuffling feature and for defining an interval of shuffling. Any suitable type of shuffling can be implemented. For example, the shuffling can be random, sequential, user-defined, or other type of shuffling.

Figure 6A:
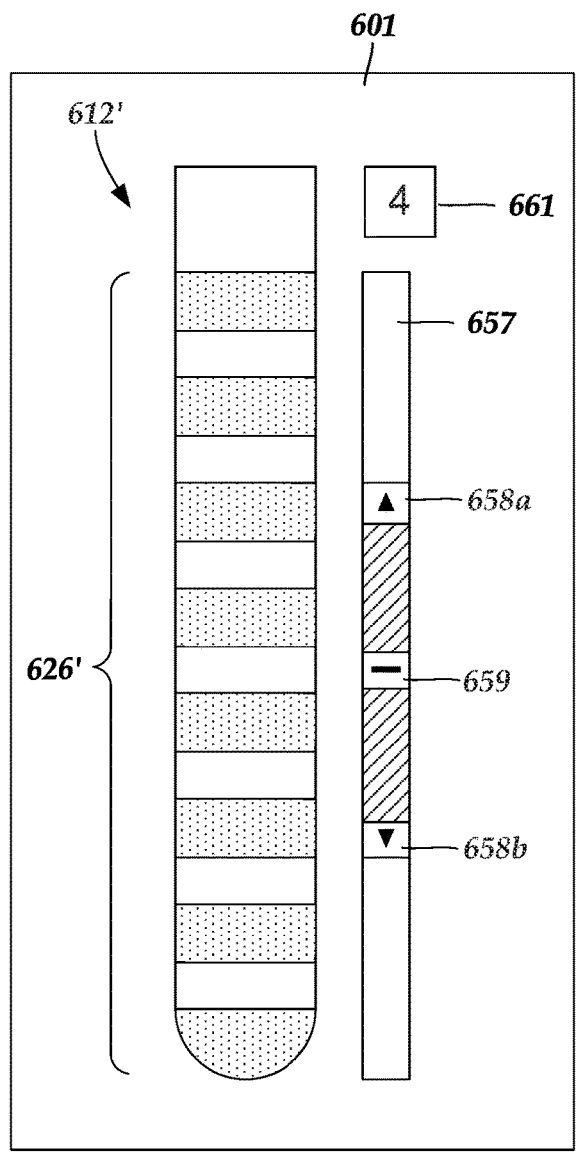
FIG. 6A is a schematic side view of one embodiment of a display showing a graphical representation of a lead with ring electrodes disposed thereon, and user-selectable controls for selecting and adjusting one or more fields obtainable from the ring electrodes, according to the invention.

Turning to FIG. 6A, in at least some embodiments each of the stimulation fields can be manually defined. A user interface can be used to provide a way for a user to define the stimulation fields individually, collectively, or both. The user interface includes user-selectable controls for adjusting the number of stimulation fields. In at least some embodiments, the user interface includes user-selectable controls for adjusting one or more field settings (e.g., which electrodes are used, whether or not current is adjusted axially or radially, the locations of the stimulation fields relative to the lead, or the like). In at least some embodiments, the user interface includes a graphical representation of one or more leads and electrodes disposed along the lead(s).

FIGS. 6A-6D show a display 601 with graphical representations of a distal portion of a lead 612' and corresponding electrodes 626'. The display 601 also includes user-selectable controls for defining fields obtainable from the electrodes 626'. Different user selections are included in each of FIGS. 6A-6D.

Figure 6B:
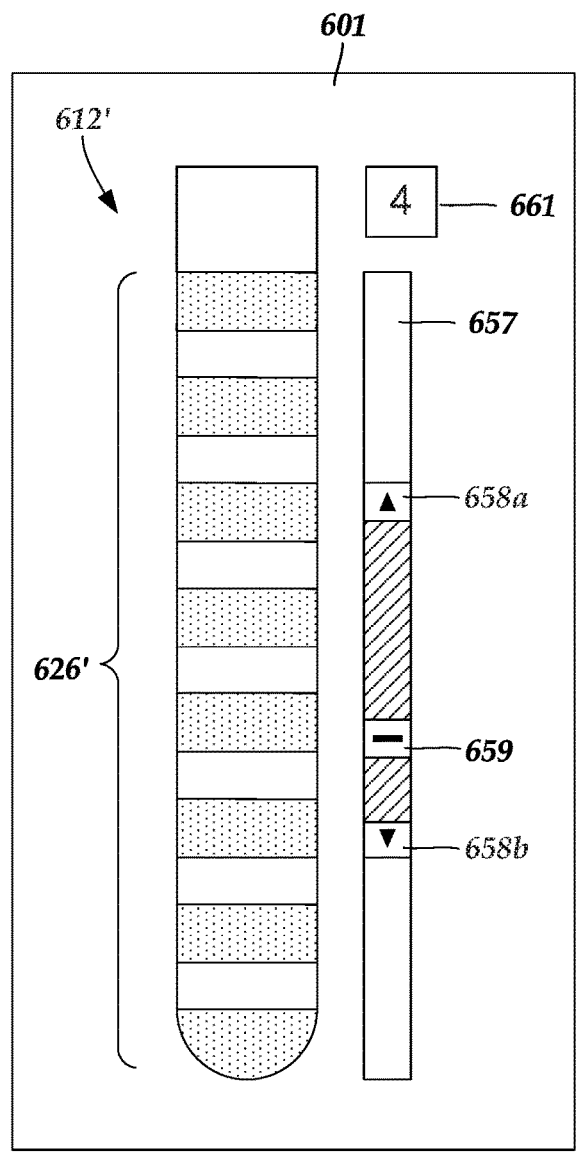
FIG. 6B is a schematic side view of a second embodiment of the display of FIG. 6A, according to the invention.
Figure 6C:
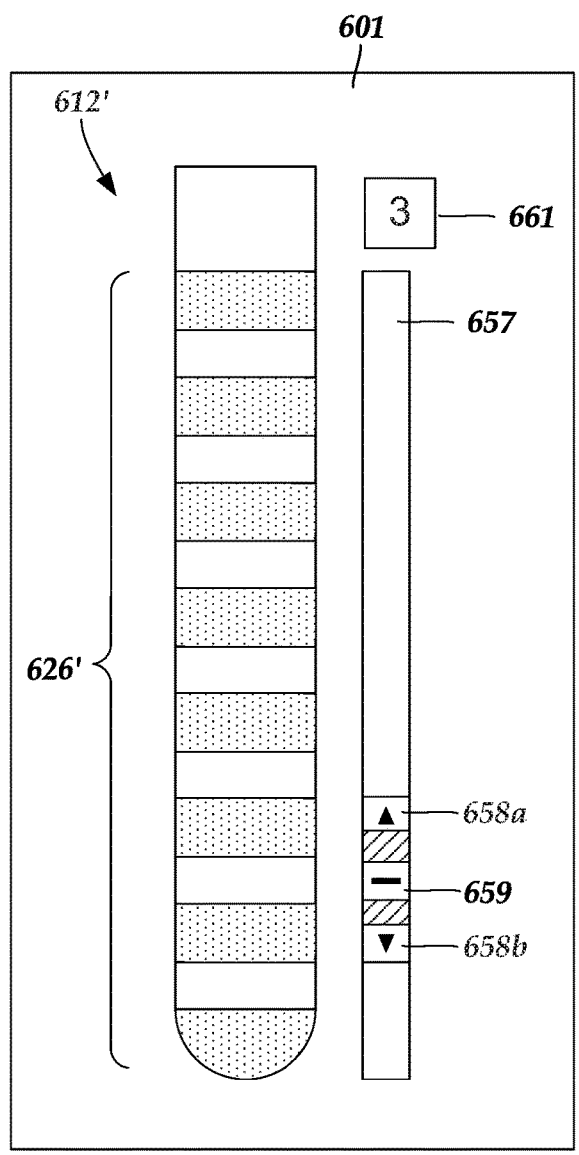
FIG. 6C is a schematic side view of a third embodiment of the display of FIG. 6A, according to the invention.
Figure 6D:
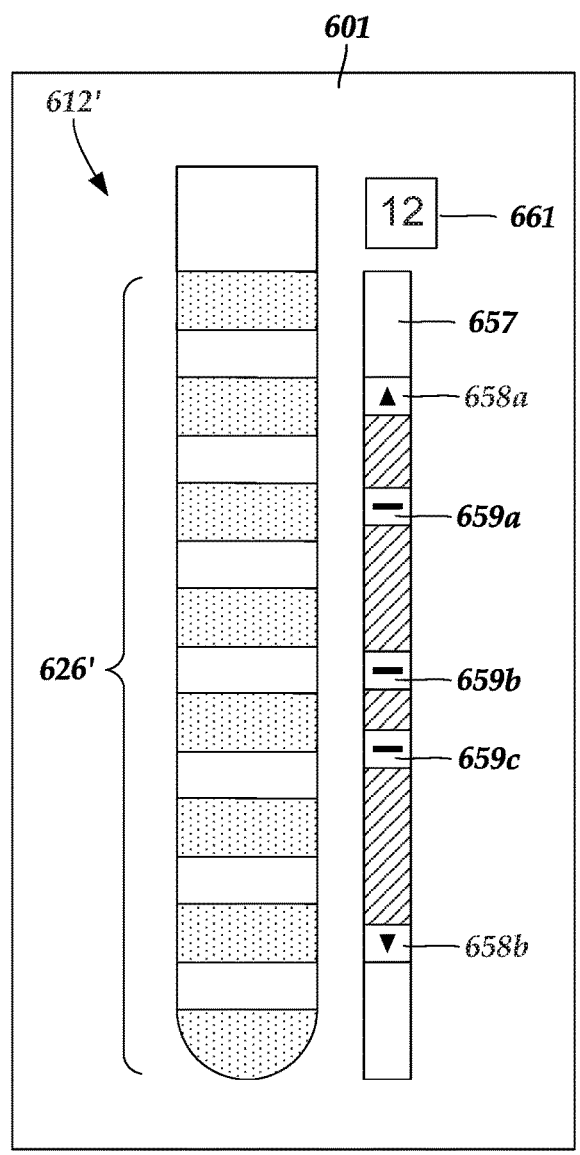
FIG. 6D is a schematic side view of a fourth embodiment of the display of FIG. 6A, according to the invention.

A user-controllable field-span indicator 657 is disposed along an electrode-containing portion of the lead 612'. The field-span indicator 657 enables a user to select the length, as well as the placement, of the span for one or more generated fields and the electrodes used to generate the field(s). The user can slide endpoints 658a and 658b to select a particular set of electrodes from which fields are generated, or a particular location along the length of the lead where one or more fields are desired. In FIGS. 6A-6D, the span is oriented axially with respect to the graphical representation of a lead 612'. In FIGS. 6A and 6B, the span covers a span of four electrodes 626'. In FIG. 6C, the span covers two electrodes. In FIG. 6D, the span covers six electrodes.

A user-selectable field control 661 enables a user to select the number of fields to be generated within the selected span. In the embodiment illustrated in FIGS. 6A and 6B, a user-selected value of "4" has been entered. In FIG. 6C, a user-selected value of "3" has been entered. In FIG. 6D, a user-selected value of "12" has been entered.

The fields are distributed along the spans. The user-controllable field-span indicator 657 includes a distribution center control 659 for selecting a position for the distribution center of the selected number of fields along the selected span. In FIGS. 6A, 6C, and 6D, the distribution center is set to a "center" of the selected span. In FIG. 6B, the distribution center is "off-center" along the span. In at least some embodiments, a span may include multiple distribution centers that can be selected by a user. FIG. 6D shows three user-adjustable distribution center controls 659a, 659b, 659c.

FIGS. 6E-6F show one embodiment of differences in field centers between a distribution center set to a "center" of a span compared to an off-center distribution center. FIG. 6E shows field centers, such as field center 663, for the fields of FIG. 6A, where the distribution center is set to the "center" of the span. As shown in FIG. 6E, the four field centers are equally spaced-apart along the span 657. FIG. 6F shows field centers, such as field center 663, for the fields of FIG. 6B, where the distribution center is off-center. As shown in FIG. 6F, the four field centers are unequally spaced-apart along the span 657.

Linear interpolation may be used to distribute the fields along the span. In at least some embodiments, field fractionalizations are generated by algorithm rather than by programmer. In at least some embodiments, fields specified by a programmer are mapped onto the user interface.

Turning to FIGS. 7A-7B, the user interface may include one or more user-selectable controls 702 for selecting between a linear (axial) set of settings of field parameters and a directional (radial) set of settings of field parameters. In some embodiments, a user can toggle between different displays, with each display being dedicated to either a linear (axial) set of settings of field parameters or a directional (radial) set of settings of field parameters. In other embodiments, a user can integrate linear and directions settings in a single display.

In FIGS. 6A-6D, the electrodes are ring-shaped. Stimulation energy emitted from ring-shaped electrodes is typically distributed evenly around a circumference of the lead. Accordingly, each field may extend around the entire circumference of the lead. Thus, while the stimulation energy can be adjusted axially, it is typically not adjustable circumferentially (i.e., radially) around a lead. When, however, electrode arrays include segmented electrodes, multiple fields can be generated circumferentially around the lead in lieu of, or in addition to, one or more linear fields.

FIGS. 7A-7B show a display 701 with a graphical representation of a distal portion of a lead 712' and corresponding electrodes 726'. A user-controllable field-span indicator 757 is disposed along an electrode-containing portion of the lead 712'.

The lead 712' and electrodes 726' are shown in two orientations. In FIG. 7A, the 712' and electrodes 726' are shown in side view, whereas in FIG. 7B, the lead 712' and electrodes 726' are shown in transverse cross-sectional view. In FIG. 7A, the span is oriented axially with respect to the lead 712', and the distribution center control 659 is adjustable linearly along the span. In FIG. 7B, the span is oriented radially with respect to the lead 712', and the distribution center control 759 is adjustable circumferentially along the span.

A user-selectable field control 761*a* enables a user to select the number of fields to be generated along the selected linear span. In the embodiment illustrated in FIG. 7A, a user-selected value of "4" has been entered. In FIG. 7B, a user-selectable field control 761*b* enables a user to select the number of fields to be generated along the selected circumferential span. In the embodiment illustrated in FIG. 7B, a user-selected value of "3" has been entered. When segmented electrodes are used, the total number of fields would typically be the number of linear fields multiplied by the number of circumferential fields. When fields are generated solely from ring electrodes, then there is only a linear component and there is no circumferential component.

Figure 8A:
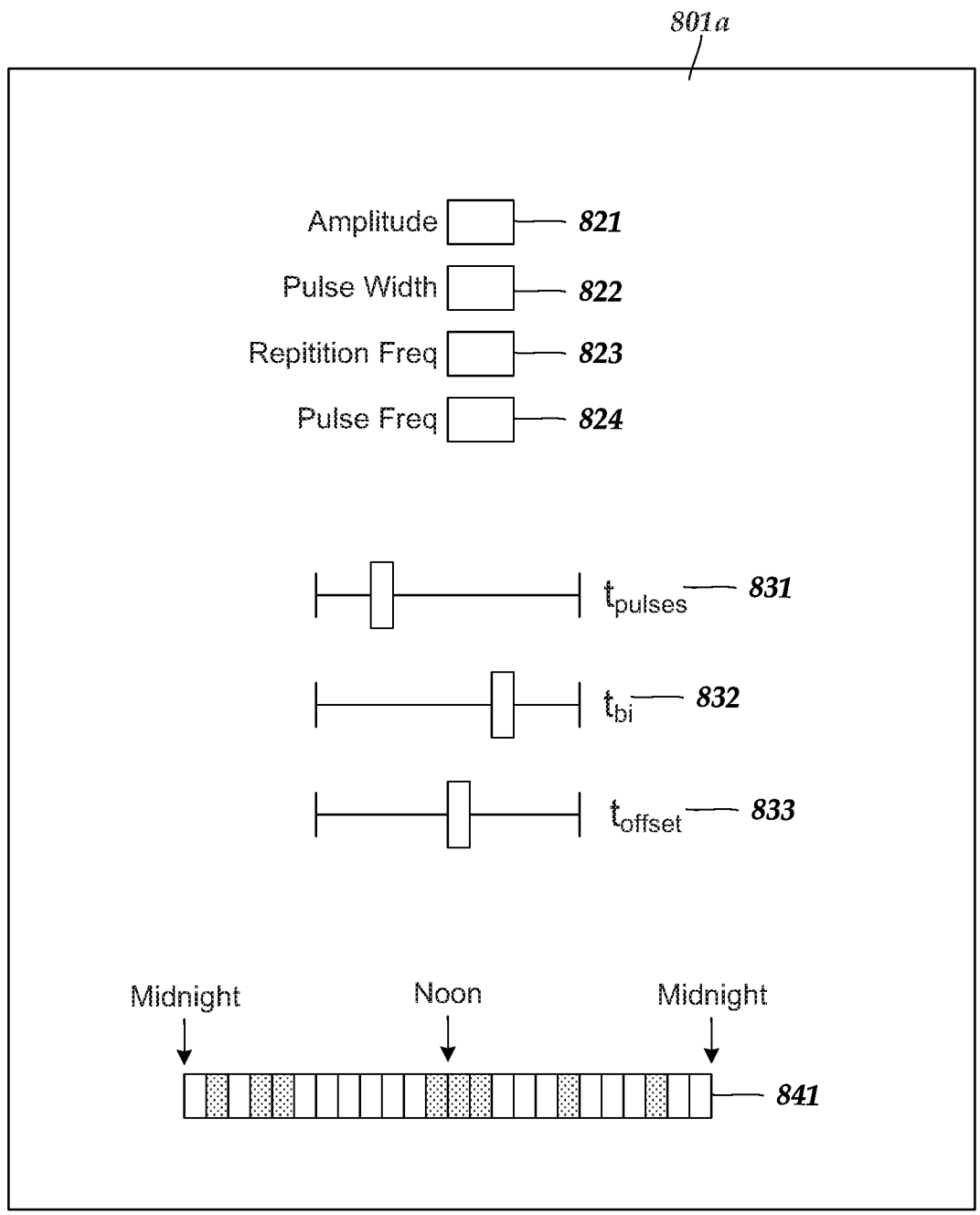
FIG. 8A is a schematic view of one embodiment of a display with user-selectable controls for adjusting stimulation parameters and time settings for each of the fields collectively, according to the invention.
Figure 8B:
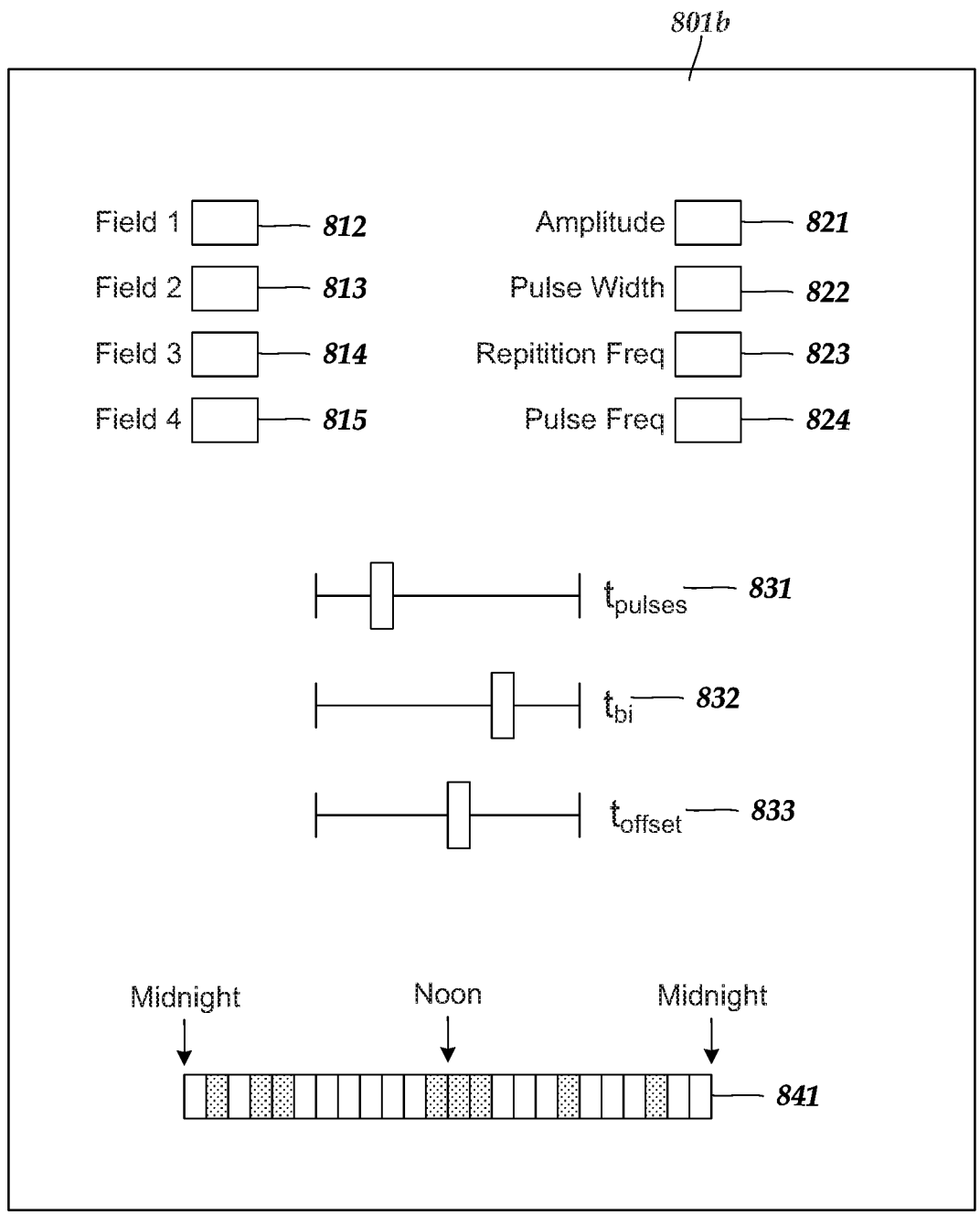
FIG. 8B is a schematic view of one embodiment of a display with user-selectable controls for adjusting stimulation parameters and time settings for each of the fields individually, according to the invention.

Turning to FIGS. 8A-8B, the user interface may include user-selectable controls for adjusting one or more stimulation parameters for each field, either separately or collectively. FIG. 8A shows a display 801*a* with user-selectable controls for selecting a general setting for making selections for each of the fields at once. In the illustrated embodiment, the user interface includes user-selectable controls 821-824 that enable a user to select values for different stimulation parameters, such as amplitude 821, pulse width 822, first frequency (see e.g., 565 in FIG. 5A) 823, and second frequency (see e.g., 526 in FIG. 5A) 824.

The user interface may include user-selectable temporal-adjustment controls for adjusting different time intervals, time delays, time offsets, or the like, for one or more fields, individually or collectively. In the illustrated embodiment, the user interface includes user-selectable controls 831-833 that enable a user to adjust the duration of time intervals, such as the first time-interval over which a series of pulses are emitted (see e.g., 524 in FIG. 5A) 831, the inter-pulse time delay (see e.g., 540 in FIG. 5A) 832, and the timing offset between different fields (see e.g., 534 in FIG. 5A) 833.

The user interface may include user-selectable temporal-adjustment controls for adjusting the timing of the repeating stimulation patterns at the micro-schedule level or over the macro-schedule level. For example, it may be desired for one or more fields to stimulate over some timing blocks, but not others. As another example, it may be desired for one or more fields to stimulate during some hours of the day, but not others. In the illustrated embodiment, the user interface includes a user-selectable control 841 that enables a user to select, for one or more fields, whether or not to stimulate over each hour of the day. It will be understood that other increments of time are possible in lieu of, or in addition to, hour increments (e.g., one minute, five minutes, ten minute, fifteen minutes, thirty minutes, two hours, four hours, or the like)

Additionally, or alternatively, the user interface may enable a user to select the same variables as described in FIG. 8A for each field individually. FIG. 8B shows a display 801*b* with user-selectable controls for selecting a general setting for making selections for each of the fields individually. In the illustrated embodiment, four fields 812-815 are available for selection. In at least some embodiments, the number of available fields is based on the number of fields available. Any suitable number of fields can be selected based on user selection or other technique.

In the illustrated embodiment, the user interface includes user-selectable controls 821-824 that enable a user to select values for different stimulation parameters, such as amplitude 821, pulse width 822, repetition frequency (see e.g., 565 in FIG. 5A) 823, and pulse frequency (see e.g., 526 in FIG. 5A) 824.

The user interface may include user-selectable temporal-adjustment controls for adjusting different time intervals for one or more fields, individually or collectively. In the illustrated embodiment, the user interface includes user-selectable controls 831-833 that enable a user to adjust the duration of time intervals, such as the first time-interval over which a series of pulses are emitted (see e.g., 524 in FIG. 5A) 831, the inter-pulse time delay (see e.g., 540 in FIG. 5A) 832, and the timing offset between different fields (see e.g., 534 in FIG. 5A) 833.

The user interface may include user-selectable temporal-adjustment controls for adjusting the timing of the repeating stimulation patterns for the fields over a period of time equal to or greater than the stimulation-pattern time interval. For example, it may be desired for one or more fields to stimulate over some timing blocks, but not others. As another example, it may be desired for one or more fields to stimulate during some hours of the day, but not others. In the illustrated embodiment, the user interface includes a user-selectable control 841 that enables a user to select, for one or more fields, whether or not to stimulate over each hour of the day.

Figure 9A:
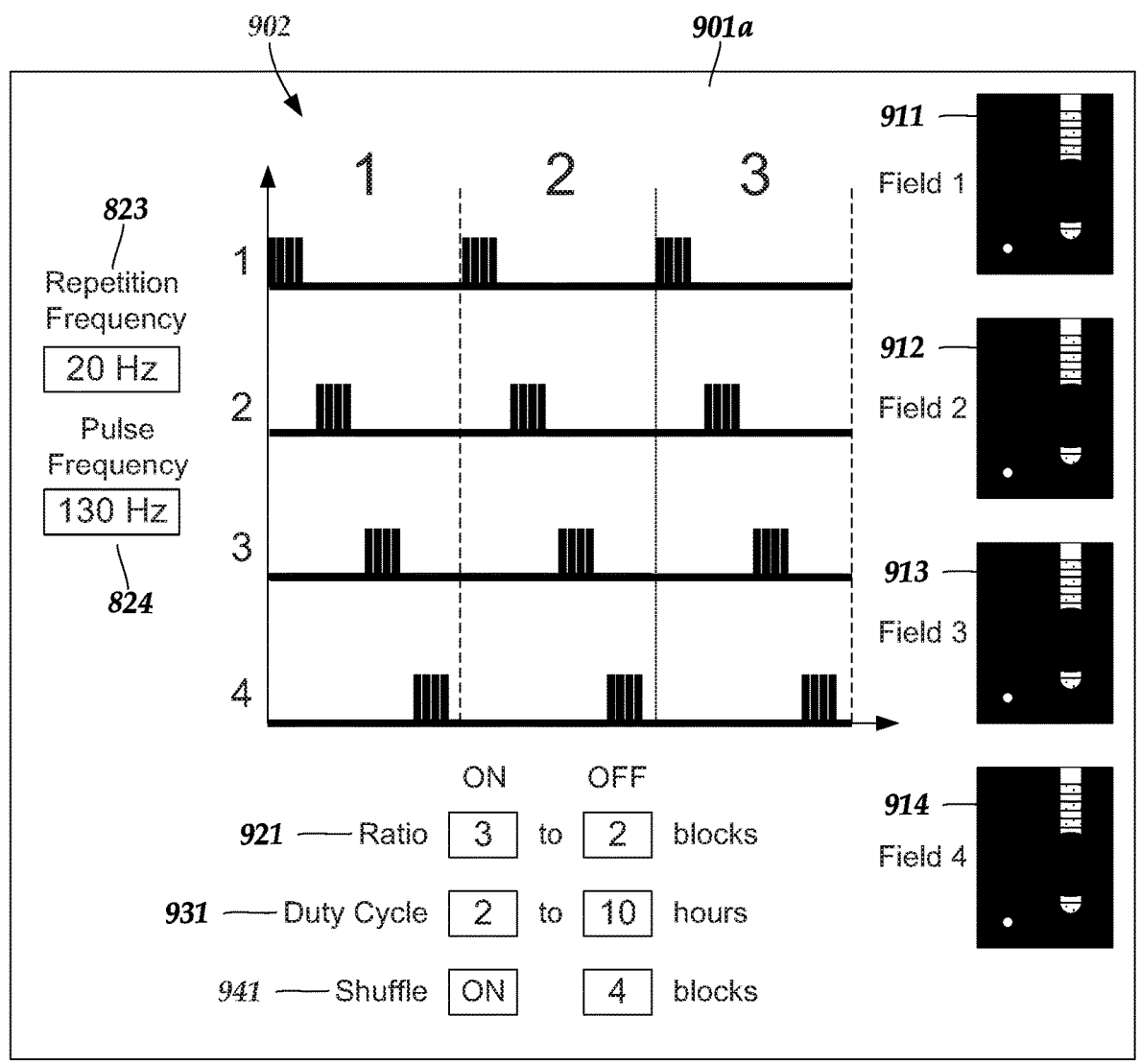
FIG. 9A is a schematic view of one embodiment of an overview display with user-selectable controls for adjusting stimulation parameters and time settings for each of the fields collectively, as well as graphical representations of stimulation patterns and fields formed from the selected settings, according to the invention.
Figure 9B:
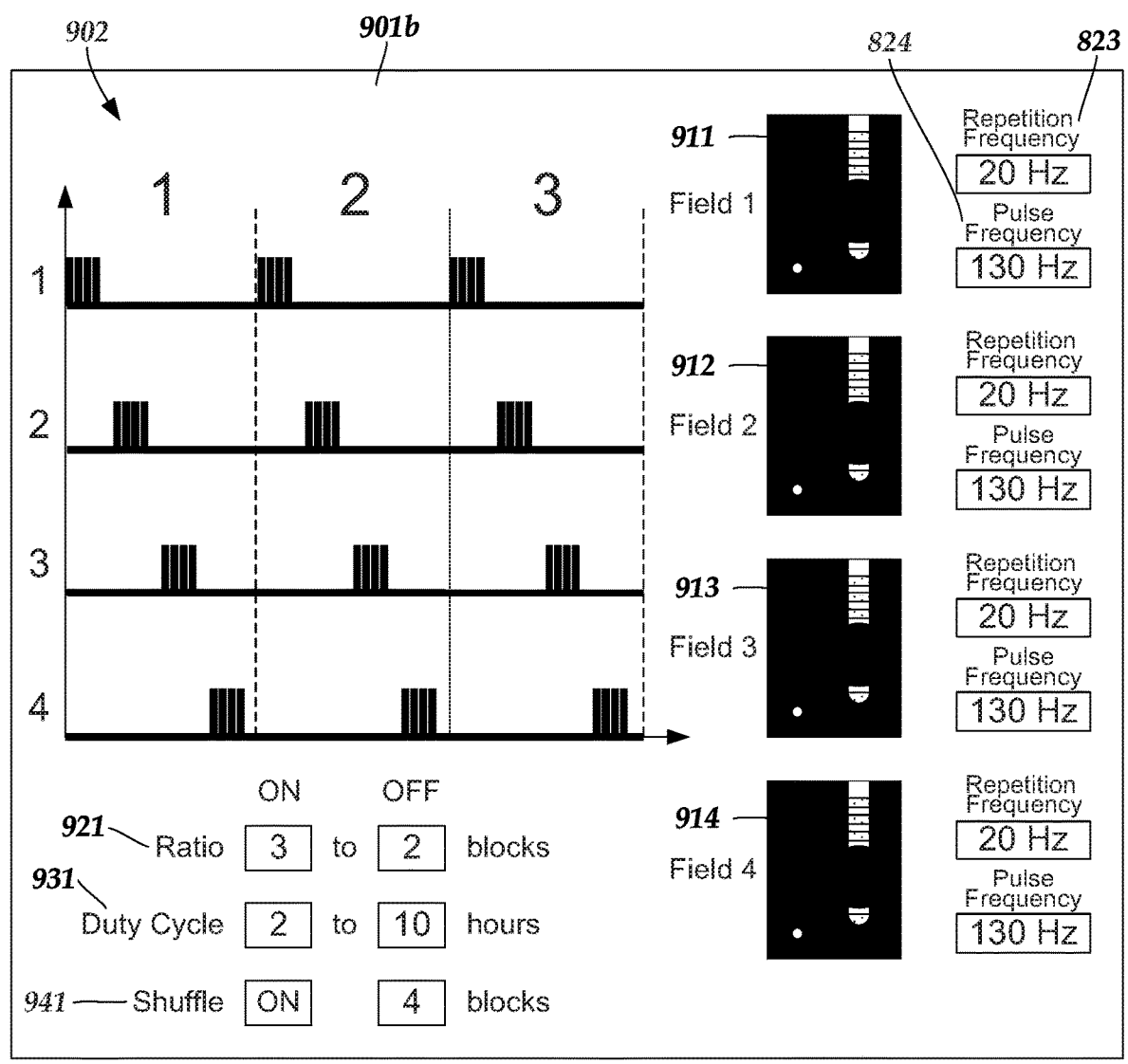
FIG. 9B is a schematic view of one embodiment of an overview display with user-selectable controls for adjusting stimulation parameters and time settings for each of the fields individually, as well as graphical representations of stimulation patterns and fields formed from the selected settings, according to the invention.

Turning to FIGS. 9A-9B, the user interface may include a display that provides an overview of previously-selected settings and one or more graphical representations of the generated fields, or stimulation patterns, or both. FIG. 9A shows a display 901*a* with a graphical representation 902 of the stimulation patterns after making selections for each of the fields collectively. The illustrated embodiment shows the stimulation patterns for four fields over three timing blocks. Each of the stimulation patterns in the illustrated embodiment are identical to one another except for a time delay between each of the fields. The user interface may include one or more stimulation-parameter settings of the graphical representations of the stimulation patterns. The illustrated embodiment shows values entered for the repetition frequency (see e.g., 565 in FIG. 5A) 823 and pulse frequency (see e.g., 526 in FIG. 5A) 824.

The user interface may include one or more graphical representations of the stimulation fields 911-914 disposed around one or more graphical representations of leads positioned in one or more orientations. The illustrated embodiment shows, for each field, a graphical representation of a stimulation field disposed around a graphical representation of a lead in both side view and transverse cross-sectional view.

The illustrated embodiment also includes several different user-selectable temporal-adjustment controls for adjusting the timing of the repeating stimulation patterns. Control 921 shows user-selected ratios for the timing blocks being in an "ON" position (i.e., stimulating) to the timing blocks being in an "OFF" position (i.e., not stimulating). In other words, the control 921 enables a user to select a repeating pattern of stimulation at the timing-block level (e.g., micro-schedule). Control 921 is selected for all of the fields collectively.

Control 931 also shows user-selected ratios of timing blocks being "ON" and "OFF". Control 931, however, shows selected repeating pattern of stimulation over a period of hours rather than over a period of timing blocks (e.g., macro-schedule). Control 931 is set for all of the fields collectively.

Control 941 enables a user to activate a field shuffle for shuffling the ordering of stimulation by the different fields. The time interval between successive reshuffles can also be user-selected (e.g., every block, after a particular number of milliseconds, after a particular number of seconds, or the like). In FIG. 9A, the time interval of reshuffling is shown as being based on a selectable number of blocks. Any suitable type of shuffling can be implemented. For example, the shuffling can be random, sequential, user-defined, or other type of shuffling. Selection of the type of shuffling can be pre-selected or user-selected, and can be performed on the display 901a, or via another device. In alternate embodiments, a slider other type of control, can be used to enable a user to select the time interval between successive reshuffles.

Additionally, or alternatively, the user interface may enable a user to select the same variables as described in FIG. 9A for each field individually. FIG. 9B shows a display 901b with a graphical representation 902 of the stimulation patterns after making selections for each of the fields collectively. The illustrated embodiment shows the stimulation patterns for four fields over three timing blocks. Each of the stimulation patterns in the illustrated embodiment are identical to one another except for a time delay between each of the fields. The user interface may include one or more stimulation-parameter settings of the graphical representations of the stimulation patterns. The illustrated embodiment shows values entered for the repetition frequency (see e.g., 565 in FIG. 5A) 823 and pulse frequency (see e.g., 526 in FIG. 5A) 824 for each individual field.

The user interface may include one or more graphical representations of the stimulation fields 911-914 disposed around one or more graphical representations of leads positioned in one or more orientations. The illustrated embodiment shows, for each field, a graphical representation of a stimulation field disposed around a graphical representation of a lead in both side view and transverse cross-sectional view.

The illustrated embodiment also includes several different user-selectable temporal-adjustment controls for adjusting the timing of the repeating stimulation patterns. Control 921 shows user-selected ratios for the timing blocks being in an "ON" position (i.e., stimulating) to the timing blocks being in an "OFF" position (i.e., not stimulating). In other words, the control 921 enables a user to select a repeating pattern of stimulation at the timing-block level. Control 921 is selected individually for each of the fields.

Control 931 also shows user-selected ratios of timing blocks being "ON" and "OFF". Control 931, however, shows selected repeating pattern of stimulation over a period of hours rather than over a period of timing blocks. Control 931 is set individually for each of the fields.

Control 941 enables a user to activate a field shuffle for shuffling the ordering of stimulation by the different fields. The time interval between successive reshuffles can also be user-selected (e.g., every block, after a particular number of milliseconds, after a particular number of seconds, or the like). In FIG. 9B, the time interval of reshuffling is shown as being based on a selectable number of blocks. Any suitable type of shuffling can be implemented. For example, the shuffling can be random, sequential, user-defined, or other type of shuffling. Selection of the type of shuffling can be pre-selected or user-selected, and can be performed on the display 901a, or via another device. In alternate embodiments, a slider other type of control, can be used to enable a user to select the time interval between successive reshuffles.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A system for programming electrical stimulation by an electrical stimulation lead, the system comprising:
 a display; and
 a processor coupled to the display and configured to:
  present an interface on the display comprising a plurality of user-selectable controls to define a plurality of stimulation fields, define, for each of the stimulation fields, a repeating stimulation pattern, and define relative timing of the repeating stimulation patterns of the stimulation fields for delivering the plurality of stimulation fields temporally-coordinated with each other, wherein the user-selectable controls comprise a field control to define the number of stimulation fields, at least one location control to define locations of the stimulation fields relative to the electrical stimulation lead, at least one repetition control to define a repetition frequency of the repeating stimulation patterns, and at least one temporal-adjustment control to define a temporal adjustment of at least one of the stimulation fields relative to another one of the stimulation fields, wherein the at least one temporal-adjustment control comprises a timing-offset control to set or adjust an offset time, $t_{offset}$ between a beginning of each of the repeating stimulation patterns for one of the stimulation fields and a beginning of each of the repeating stimulation patterns for another one of the stimulation fields,
  receive selections of the user-selectable controls to define the plurality of stimulation fields and the repeating stimulation patterns, and initiate a signal that provides a pulse generator with instructions that enable the pulse generator to generate the plurality of defined stimulation fields according to the repeating stimulation patterns using the electrical stimulation lead coupled to the pulse generator.

2. The electrical stimulation system of claim 1 wherein the plurality of user-selectable controls further comprises a first time-interval control to set or adjust a first time period, $t_{pulses}$, over which a series of pulses of the stimulation fields are to be emitted.

3. The electrical stimulation system of claim 2 wherein the first time-interval control is configured for collective setting or adjustment of the first time period for all of the stimulation fields.

4. The electrical stimulation system of claim 2 wherein, the first time-interval control is configured for separate setting or adjustment of the first time period for each of the stimulation fields.

5. The electrical stimulation system of claim 2, wherein the at least one temporal-adjustment control also enables adjustment of a repetition frequency for the repeating stimulation pattern for each stimulation field of the plurality of stimulation fields.

6. The electrical stimulation system of claim 2, wherein the plurality of user-selectable controls further comprises an inter-pulse time delay control to set or adjust an inter-pulse time delay, $t_{iptd}$, between an end of the first time period of a first stimulation field of the plurality of stimulation fields and a beginning of the first time period of a second stimulation field of the plurality of stimulation fields.

7. The electrical stimulation system of claim 2, wherein the interface further comprises a graphical representation of the repeating stimulations pattern for each of the plurality of stimulation fields arranged into a set of repeating time blocks of equal duration to one another, wherein each time block represents the first time period.

8. The electrical stimulation system of claim 7, wherein the interface further comprises a user-selectable control for selecting, for each time block of the set of repeating time blocks, whether or not each stimulation field of the plurality of stimulation fields is stimulating patient tissue.

9. The electrical stimulation system of claim 7, wherein the interface further comprises a user-selectable control for selecting, for increments of time greater than a time block of the set of repeating time blocks, whether or not each stimulation field of the plurality of stimulation fields is stimulating patient tissue.

10. The electrical stimulation system of claim 2, further comprising a user-selectable control for selecting pulse frequencies for the series of pulses emitted over the first time period.

11. The electrical stimulation system of claim 1, wherein the at least one location control enables selection of a subset of a plurality of electrodes of the stimulation lead for generating the plurality of stimulation fields.

12. The electrical stimulation system of claim 11, wherein the at least one location control enables selection of a field center for the selected subset of the plurality of electrodes for generating the plurality of stimulation fields.

13. The electrical stimulation system of claim 11, wherein the at least one location control enables selection of locations of the stimulation fields relative to the electrical stimulation lead both linearly and circumferentially with respect to the electrical stimulation lead.

14. The electrical stimulation system of claim 1, further comprising the electrical stimulation lead configured and arranged for implantation into a patient, the electrical stimulation lead comprising:
a lead body having a proximal portion and a distal portion; and
a plurality of electrodes disposed along the distal portion of the lead body.

15. The electrical stimulation system of claim 14, further comprising the pulse generator coupleable to the electrical stimulation lead, the pulse generator configured and arranged for providing electrical stimulation signals to the plurality of electrodes for stimulation of patient tissue.

16. A non-transitory computer-readable medium having processor-executable instructions for programming electrical stimulation by an electrical stimulation lead, the processor-executable instructions when installed onto a device enable the device to perform actions comprising:
generating, for display, an interface comprising a plurality of user-selectable controls to define a plurality of stimulation fields for the electrical stimulation lead, define, for each of the stimulation fields, a repeating stimulation pattern, and define relative timing of the repeating stimulation patterns of the stimulation fields for delivering the plurality of stimulation fields temporally-coordinated with each other, wherein the user-selectable controls comprise a field control to define the number of stimulation fields, at least one location control to define locations of the stimulation fields relative to the electrical stimulation lead, at least one repetition control to define a repetition frequency of the repeating stimulation patterns, and at least one temporal-adjustment control to define a temporal adjustment of at least one of the stimulation fields relative to another one of the stimulation fields, wherein the at least one temporal-adjustment control comprises a timing-offset control to set or adjust an offset time, $t_{offset}$, between a beginning of each of the repeating stimulation patterns for one of the stimulation fields and a beginning of each of the repeating stimulation patterns for another one of the stimulation fields;
receiving selections of the user-selectable controls to define the plurality of stimulation fields and the repeating stimulation patterns; and
initiating a signal that provides a pulse generator with instructions that enable the pulse generator to generate the plurality of defined stimulation fields according to the repeating stimulation patterns using the electrical stimulation lead coupled to the pulse generator.

17. The non-transitory computer-readable medium of claim 16, wherein the plurality of user-selectable controls further comprises a first time-interval control to set a first time period, $t_{pulses}$, over which a series of pulses of the stimulation fields are to be emitted.

18. The non-transitory computer-readable medium of claim 17, wherein the plurality of user-selectable controls further comprises an inter-pulse time delay control to set or adjust an inter-pulse time delay, $t_{iptd}$, between an end of the first time period of a first stimulation field of the plurality of stimulation fields and a beginning of the first time period of a second stimulation field of the plurality of stimulation fields.

19. The non-transitory computer-readable medium of claim 17, wherein the interface further comprises a graphical representation of the repeating stimulations pattern for each of the plurality of stimulation fields arranged into a set of repeating time blocks of equal duration to one another, wherein each time block represents the first time period.

20. A method for providing electrical stimulation using a plurality of stimulation fields, with each of the plurality of stimulation fields having a repeating stimulation pattern, the method comprising:

advancing an electrical stimulation lead to a target parenchymal population within a patient, the electrical stimulation lead comprising a plurality of electrodes;

coupling the electrical stimulation lead to a pulse generator configured and arranged for providing electrical stimulation signals to the plurality of electrodes for stimulation of patient tissue; and using the electrical stimulation system of claim 1 for initiating the signal that provides the pulse generator with instructions that enable the pulse generator to generate the plurality of defined stimulation fields according to the stimulation patterns using the electrical stimulation lead.

* * * * *